(12) United States Patent
Akahata et al.

(10) Patent No.: US 12,134,777 B2
(45) Date of Patent: Nov. 5, 2024

(54) ALPHAVIRUS REPLICON VECTOR AND IMMUNOTHERAPY BY ADMINISTERING SAME

(71) Applicant: VLP Therapeutics, Inc., Wilmington, DE (US)

(72) Inventors: Wataru Akahata, Kensington, MD (US); Jonathan F. Smith, Redwood City, CA (US)

(73) Assignee: VLP Therapeutics, Inc., Wilmington, DE (US)

( * ) Notice: Subject to any disclaimer, the term of this patent is extended or adjusted under 35 U.S.C. 154(b) by 356 days.

(21) Appl. No.: 17/242,916

(22) Filed: Apr. 28, 2021

(65) Prior Publication Data

US 2021/0340567 A1   Nov. 4, 2021

Related U.S. Application Data

(60) Provisional application No. 63/017,993, filed on Apr. 30, 2020.

(51) Int. Cl.
| | | |
|---|---|---|
| *C12N 15/86* | (2006.01) | |
| *A61K 9/48* | (2006.01) | |
| *A61K 9/51* | (2006.01) | |
| *A61P 35/00* | (2006.01) | |
| *C07K 14/54* | (2006.01) | |
| *A61K 38/00* | (2006.01) | |

(52) U.S. Cl.
CPC ............ *C12N 15/86* (2013.01); *A61K 9/4825* (2013.01); *A61K 9/5123* (2013.01); *A61P 35/00* (2018.01); *C07K 14/5434* (2013.01); *A61K 38/00* (2013.01); *C12N 2770/36143* (2013.01)

(58) Field of Classification Search
None
See application file for complete search history.

(56) References Cited

U.S. PATENT DOCUMENTS

| | | |
|---|---|---|
| 5,185,440 A | 2/1993 | Davis et al. |
| 5,439,809 A | 8/1995 | Haynes et al. |
| 5,505,947 A | 4/1996 | Johnston et al. |
| 5,580,773 A | 12/1996 | Kang et al. |
| 5,629,204 A | 5/1997 | Honjo et al. |
| 5,639,650 A | 6/1997 | Johnston et al. |
| 5,643,576 A | 7/1997 | Johnston et al. |
| 5,698,520 A | 12/1997 | Honjo et al. |
| 5,792,462 A | 8/1998 | Johnston et al. |
| 5,811,407 A | 9/1998 | Johnston et al. |
| 5,939,598 A | 8/1999 | Kucherlapati et al. |
| 6,008,035 A | 12/1999 | Johnston et al. |
| 6,156,558 A | 12/2000 | Johnston et al. |
| 6,521,235 B2 | 2/2003 | Johnston et al. |
| 6,531,135 B1 | 3/2003 | Johnston et al. |
| 6,541,010 B1 | 4/2003 | Johnston et al. |
| 6,583,121 B1 | 6/2003 | Johnston et al. |
| 6,783,939 B2 | 8/2004 | Olmsted |
| 6,844,188 B1 | 1/2005 | Macdonald et al. |
| 6,982,087 B2 | 1/2006 | Johnston et al. |
| 7,045,335 B2 | 5/2006 | Smith et al. |
| 7,078,218 B2 | 7/2006 | Smith et al. |
| 7,101,550 B2 | 9/2006 | Wood et al. |
| 7,235,235 B2 | 6/2007 | Johnston et al. |
| 7,419,674 B2 | 9/2008 | Chulay et al. |
| 7,425,337 B2 | 9/2008 | Smith et al. |
| 7,442,381 B2 | 10/2008 | Smith et al. |
| 7,531,180 B2 | 5/2009 | Polo et al. |
| 7,572,453 B2 | 8/2009 | Polo et al. |
| 7,595,048 B2 | 9/2009 | Honjo et al. |
| 7,790,181 B2 | 9/2010 | Platteborze et al. |
| 8,158,418 B2 | 4/2012 | Polo et al. |
| 8,263,092 B1 | 9/2012 | Smith et al. |
| 8,460,913 B2 | 6/2013 | Kamrud et al. |
| 8,617,533 B2 | 12/2013 | Smith et al. |
| 8,680,258 B2 | 3/2014 | Coffield et al. |
| 8,709,441 B2 | 4/2014 | Rayner et al. |
| 9,079,943 B2 | 7/2015 | Rayner et al. |
| 9,187,729 B2 | 11/2015 | Depaz et al. |
| 9,249,191 B2 | 2/2016 | Ueno et al. |
| 9,255,126 B2 | 2/2016 | Polo et al. |
| 9,353,353 B2 | 5/2016 | Nabel et al. |
| 9,363,353 B1 | 6/2016 | Chik |
| 9,416,370 B2 | 8/2016 | Smith et al. |
| 9,441,247 B2 | 9/2016 | Rayner et al. |
| 9,487,563 B2 | 11/2016 | Nabel et al. |
| 9,512,190 B2 | 12/2016 | Ueno et al. |

(Continued)

FOREIGN PATENT DOCUMENTS

| | | | |
|---|---|---|---|
| AU | 2007317347 A1 * | 5/2009 | ............ A61K 39/12 |
| CN | 102321639 A | 1/2012 | |

(Continued)

OTHER PUBLICATIONS

International Search Report and Written Opinion, dated Jul. 27, 2021, issued in International Application No. PCT/JP2021/017078.
Wataru Akahata et al., "A VLP vaccine for epidemic Chikungunya virus protects non-human primates against infection," Nat. Med., 2010, 16(3); 334-338. (pp. 1-12).
Ira Mellman et al., "Cancer immunotherapy comes of age," Nature, 2011, vol. 480 (pp. 480-489).
António Roldão et al., "Virus-like particles in vaccine development", Expert Rev. Vaccines, 2010, 9(10):, pp. 1149-1176.

(Continued)

*Primary Examiner* — Jennifer Chin
(74) *Attorney, Agent, or Firm* — Sughrue Mion, PLLC

(57) ABSTRACT

Provided herein is a novel immunologically-active alphavirus replicon vector which comprises a nucleic acid encoding alphavirus nonstructural proteins nsp1-4 and a cytokine protein(s)/polypeptide(s), which is useful for the treatment of a cancer and/or an inflammatory disease.

17 Claims, 7 Drawing Sheets
Specification includes a Sequence Listing.

(56) References Cited

U.S. PATENT DOCUMENTS

| | | |
|---|---|---|
| 9,597,414 B2 | 3/2017 | Coffield, III et al. |
| 9,637,532 B2 | 5/2017 | Akahata et al. |
| 9,969,986 B2 | 5/2018 | Akahata et al. |
| 10,098,943 B2 | 10/2018 | Akahata et al. |
| 10,111,943 B2 | 10/2018 | Smith et al. |
| 10,434,187 B2 | 10/2019 | Coffield, III et al. |
| 2003/0108521 A1 | 6/2003 | Calatrava |
| 2003/0232324 A1 | 12/2003 | Polo et al. |
| 2005/0214321 A1 | 9/2005 | Rasochova et al. |
| 2007/0122378 A1 | 5/2007 | Freeman et al. |
| 2008/0025067 A1 | 1/2008 | Scheuerlein |
| 2009/0079185 A1 | 3/2009 | Carbines-Evans et al. |
| 2009/0298955 A1 | 12/2009 | Handa et al. |
| 2009/0305950 A1 | 12/2009 | Minato et al. |
| 2009/0312190 A1 | 12/2009 | Chinea Santiago et al. |
| 2011/0027306 A1 | 2/2011 | Rayner et al. |
| 2011/0035004 A1 | 2/2011 | Maxwell |
| 2011/0081341 A1 | 4/2011 | Honjo et al. |
| 2011/0207223 A1 | 8/2011 | Tang et al. |
| 2011/0262389 A1 | 10/2011 | Mosco |
| 2011/0318373 A1 | 12/2011 | Sasikumar et al. |
| 2012/0003266 A1 | 1/2012 | Nable et al. |
| 2013/0122262 A1 | 5/2013 | Nagakura et al. |
| 2013/0251744 A1 | 9/2013 | Ueno et al. |
| 2014/0120125 A1 | 5/2014 | Ella et al. |
| 2014/0127247 A1 | 5/2014 | Dubensky, Jr. et al. |
| 2014/0170186 A1 | 6/2014 | Nabel et al. |
| 2014/0363458 A1 | 12/2014 | Ueno et al. |
| 2015/0017194 A1 | 1/2015 | Akahata et al. |
| 2016/0040134 A1 | 2/2016 | Akahata et al. |
| 2016/0074501 A1 | 3/2016 | Akahata et al. |
| 2016/0090403 A1 | 3/2016 | Ueno et al. |
| 2016/0200775 A1 | 7/2016 | Akahata et al. |
| 2016/0303221 A1 | 10/2016 | Nabel et al. |
| 2017/0035871 A1 | 2/2017 | Ueno et al. |
| 2017/0065703 A1 | 3/2017 | Akahata et al. |
| 2017/0233450 A1 | 8/2017 | Akahata et al. |
| 2017/0252425 A1 | 9/2017 | Akahata et al. |
| 2019/0185822 A1 | 6/2019 | Akahata et al. |

FOREIGN PATENT DOCUMENTS

| | | | |
|---|---|---|---|
| CN | 106085974 A | 11/2016 | |
| JP | 4-506301 A | 11/1992 | |
| JP | 2007-512842 A | 5/2007 | |
| JP | 2007-537761 A | 12/2007 | |
| JP | 2008-543774 A | 12/2008 | |
| WO | 93/10152 A1 | 5/1993 | |
| WO | 96/37616 A1 | 11/1996 | |
| WO | 97/12048 A1 | 4/1997 | |
| WO | 99/18226 A2 | 4/1999 | |
| WO | 99/41383 A1 | 8/1999 | |
| WO | 02/096939 A2 | 12/2002 | |
| WO | 03/102166 A2 | 12/2003 | |
| WO | 2004/043399 A2 | 5/2004 | |
| WO | 2004/085660 A2 | 10/2004 | |
| WO | 2006/040334 A1 | 4/2006 | |
| WO | 2006/088229 A1 | 8/2006 | |
| WO | 2007/003384 A1 | 1/2007 | |
| WO | 2007/059715 A2 | 5/2007 | |
| WO | 2007/100098 A1 | 9/2007 | |
| WO | 2008/025067 A1 | 3/2008 | |
| WO | 2009/079185 A2 | 6/2009 | |
| WO | 2010/062396 A2 | 6/2010 | |
| WO | 2011/035004 A1 | 3/2011 | |
| WO | 2012/006180 A1 | 1/2012 | |
| WO | 2012/023995 A1 | 2/2012 | |
| WO | 2012/106356 A2 | 8/2012 | |
| WO | 2012/123755 A1 | 9/2012 | |
| WO | 2012/172574 A1 | 12/2012 | |
| WO | 2013/009884 A1 | 1/2013 | |
| WO | 2013/063248 A1 | 5/2013 | |
| WO | 2013/122262 A1 | 8/2013 | |
| WO | 2013/151764 A1 | 10/2013 | |
| WO | WO-2014170493 A2 * | 10/2014 | ............. C12N 15/86 |
| WO | 2015/005500 A1 | 1/2015 | |
| WO | 2015/139784 A1 | 9/2015 | |
| WO | 2016/021209 A1 | 2/2016 | |
| WO | 2016/048903 A1 | 3/2016 | |
| WO | 2016/109792 A2 | 7/2016 | |
| WO | 2016/199936 A1 | 12/2016 | |
| WO | 2016/210127 A1 | 12/2016 | |
| WO | 2017/009873 A1 | 1/2017 | |
| WO | 2017/015463 A2 | 1/2017 | |
| WO | 2018/068008 A1 | 4/2018 | |
| WO | 2018/213731 A1 | 11/2018 | |
| WO | 2019/124441 A1 | 6/2019 | |

OTHER PUBLICATIONS

Gunther Spohn et al., "A Virus-Like Particle-Based Vaccine Selectively Targeting Soluble TNF-α Protects from Arthritis without Inducing Reactivation of Latent Tuberculosis", The Journal of Immunology, 2007, 178: pp. 7450-7457.

Elizabeth V.L. Grgacic et al., "Virus-like particles: Passport to immune recognition", Methods, 2006, 40: pp. 60-65.

Gary T. Jennings et al., "Immunodrugs: Therapeutic VLP-Based Vaccines for Chronic Diseases", Annu. Rev. Pharmacol. Toxicol., 2009, 49: pp. 303-326.

Heinz Leibl et al., "Adjuvant/carrier activity of inactivated tick-borne encephalitis virus", Vaccine, 1998, 16(4): pp. 340-345.

Bryce Chackerian et al., "Determinants of Autoantibody Induction by Conjugated Papillomavirus Virus-Like Particles", The Journal of Immunology, 2002, 169: pp. 6120-6126.

Maria Lia Palomba et al., "CD8+ T-Cell-Dependent Immunity Following Xenogeneic DNA Immunization against CD20 in a Tumor Challenge Model of B-Cell Lymphoma", Clinical Cancer Research, 2005, 370(11): pp. 370-379.

Wendy K. Roberts et al., "Vaccination with CD20 peptides induces a biologically active, specific immune response in mice", Blood, 2002, 99: pp. 3748-3755.

Kathy D. McCoy et al., "Cytotoxic T Lymphocyte-associated Antigen 4 (CTLA-4) Can Regulate Dendritic Cell-induced Activation and Cytotoxicity of CD8+ T Cells Independently of CD4+ T Cell Help", J. Exp. Med., 1999, 189(7): pp. 1157-1162.

Gregory J. Atkins et al., "Therapeutic and prophylactic applications of alphavirus vectors", Expert Reviews in Molecular Medicine, 2008, 10(e33): pp. 1-17.

Akahata W., and G.J. Nabel, 2012, "A specific domain of the Chikungunya virus E2 protein regulates particle formation in human cells: implications for alphavirus vaccine design," J. Virol. 86(16): pp. 8879-8883.

Kuo, S. -C., et al., 2012, Cell-based analysis of Chikungunya virus E1 protein in membrane fusion, J. Biomed. Sci. 19(44): pp. 1-12.

Siyang Sun et al: "Structural analyses at pseudo atomic resolution of Chikungunya virus and antibodies show mechanisms of neutralization", eLIFE, Apr. 2, 2013, vol. 2, pp. 1-27.

Carvalho et al., "Malaria Vaccine: Candidate Antigens, Mechanisms, Constraints and Prospects," Scand. J. Immunol., Blackwell Science Ltd. Jul. 1, 2002, vol. 56, pp. 327-343.

Crompton et al., "Advances and Challenges in malaria vaccine development," Science in medicine, The Journal of Clinical Investigation, Dec. 2010, vol. 120, No. 12, pp. 4168-4178.

Malaria Vaccine Program, http://www.globalvaccines.org/content/malaria+vaccine+program/19614, 4 pages total (2012).

Rodriguez D et al., Vaccine Efficacy against malaria by the Combination of Porcine Parvovirus-Like Particles and Vaccinia Virus Vectors Expressing CS of Plasmodium, PLoS One, Apr. 17, 2012, vol. 7, No. 4, e34445. (pp. 1-10).

Oliveira GA et al., Safety and enhanced immunogenicity of a Hepatitis B core particle Plasmodium falciparum Malaria vaccine formulated in adjuvant montanide ISA 720 in a Phase I Trial, Infect. Immun., 2005, vol. 73, No. 6, pp. 3587-3597.

Jones RM et al., A plant-produced Pfs25 VLP Malaria Vaccine Candidate Induces Persistent Transmission Blocking Antibodies against Plasmodium falciparum in immunized mice, PLoS One, Nov. 18, 2013, vol. 8, No. 11, e79538, pp. 1-10, doi:10.1371/journal.pone.0079538.

(56) References Cited

OTHER PUBLICATIONS

Rodrigues M et al., Influenza and Vaccinia viruses expressing Malaria CD8+T and B Cell epitopes. Comparison of their immunogenicity and capacity to induce protective immunity, J. Immunol., 1994, vol. 153, No. 10, pp. 4636-4648. (15 pages).
Pfeiffer B et al., A virosome-mimotope approach to synthetic vaccine design and optimization: synthesis, conformation, and immune recognition of a potential Malaria-vaccine candidate, Angew. Chem. Int. Ed., 2003, vol. 42, No. 21, pp. 2368-2371. (5 pages).
Ghasparian A et al., Engineered synthetic virus-like particles and their use in vaccine delivery, Chembiochem, 2011, vol. 12, No. 1, pp. 100-109.
Dobano C et al., Alphavirus replicon particles are highly immunogenic in the murine Malaria model by homologous or heterologous immunization, Open Vaccine Journal, vol. 1, 2008, pp. 27-37.
Lechner F et al., Virus-like particles as a modular system for novel vaccines, Intervirology, 2002, vol. 45, No. 4-6, pp. 212-217.
Gilbert SC et al., A protein particle vaccine containing multiple Malaria epitopes, Nat. Biotechnol., 1997, vol. 15, No. 12, pp. 1280-1284. (7 pages).
Allsopp CE et al., "Comparison of numerous delivery systems for the induction of cytotoxic T lymphocytes by immunization," Eur. J. Immunol., 1996, vol. 26, No. 8, pp. 1951-1959.
Oliveira-Ferreira et al., "Immunogenicity of Ty-VLP bearing a CD8(+) T cell epitope of the CS protein of P. yoelii: enhanced memory response by boosting with recombinant vaccinia virus.", Vaccine. Mar. 6, 2000; 18(17); 1863-1869.
GenBank: AAW78190.1. circumsporozoite protein, partial [Plasmodium falciparum]. Dec. 29, 2006. (2 pages).
Gregson et al., "Phase 1 Trial of an Alhydrogel Adjuvanted Hepatitis B Core Virus-Like Particle Containing Epitopes of Plasmodium falciparum Circumsporozoite Protein.", PLoS ONE. Feb. 2008 | vol. 3 | Issue 2| e1556, pp. 1-9.
Adams et al., "The expression of hybrid HIV: Ty virus-like particles in yeast," Nature Sep. 3-9, 1987; 329(6134); pp. 68-70. (3 pages).
Federico M., "Virus-like particles show promise as candidates for new vaccine strategies," Future Virol. (2010) 5(4); pp. 371-374.
Birkett A et al. "A Modified Hepatitis B Virus Core Particle Containing Multiple Epitopes of the Plasmodium falciparum Circumsporozoite Protein Provides a Highly Immunogenic Malaria Vaccine in Preclinical Analyses in Rodent and Primate Hosts", Infection and Immunity, American Society for Microbiology, US, vol. 70, No. 12; Dec. 1, 2002, pp. 6860-6870.
Milich D R et al. "Conversion of poorly immunogenic malaria repeat sequences into a highly immunogenic vaccine candidate", Vaccine, Elsevier Ltd, GB; vol. 20, No. 5-6; Dec. 12, 2001; pp. 771-788.
Shiratsuchi T. et al. "Replacing adenoviral vector HVR1 with a malaria B cell epitope improves immunogenicity and circumvents preexisting immunity to adenovirus in mice", Journal of Clinical Investigation; vol. 120, No. 10; Oct. 2010; pp. 3688-3701.
Y. Agata et al., "Expression of the PD-1 antigen on the surface of stimulated mouse T and B lymphocytes," International Immunology, 1996, vol. 8, No. 5, pp. 765-772.
F. Notka et al., "Accelerated clearance of SHIV in rhesus monkeys by virus-like particle vaccines is dependent on induction of neutralizing antibodies", Vaccine, 2000, vol. 18, No. 3-4, p. 291-301.
U. Arora et al., "Virus-like particles displaying envelope domain III of dengue virus type 2 induce virus-specific antibody response in mice", Vaccine, Jan. 2013, vol. 31, No. 6, p. 873-878.
Rodion Gorchakov et al., "Comparative analysis of the alphavirus-based vectors expressing Rift Valley fever virus glycoproteins," Virology, vol. 366 (2007), pp. 212-225.
Sigrid Elshuber et al., "Cleavage of protein prM is necessary for infection of BHK-21 cells by tick-borne encephalitis virus," Journal of General Virology (2003) vol. 84, pp. 183-191.
Simona Ozden et al., "Inhibition of Chikungunya Virus Infection in Cultured Human Muscle Cells by Furin Inhibitors," Journal of Biological Chemistry, vol. 283, No. 32, Aug. 8, 2008 (10 pages total).
Sigrid Elshuber et al., "Resuscitating Mutations in a Furin Cleavage-Deficient Mutant of the Flavivirus Tick-Borne Encephalitis Virus," Journal of Virology, vol. 79, No. 18, Sep. 2005, p. 11813-11823.
Hevey et al., "Marburg Virus Vaccines Based upon Alphavirus Replicons Protect Guinea Pigs and Nonhuman Primates", Virology, 251: 28-37 (1998).
Bonaldo et al., "Surface Expression of an Immunodominant Malaria Protein B Cell Epitope by Yellow Fever Virus", J. Mol. Biol., 315(4):873-885 (2002).
Vuola et al., "Differential Immunogenicity of Various Heterologous Prime-Boost Vaccine Regimens Using DNA and Viral Vectors in Healthy Volunteers", J. Immunol., 174(1):449-455 (2005).
Calvo-Calle et al., "A Linear Peptide Containing Minimal T- and B-Cell Epitopes of Plasmodium falciparum Circumsporozoite Protein Elicits Protection against Transgenic Sporozoite Challenge", Infection and Immunity, Dec. 2006. Vol. 74, No. 12. p. 6929-6939.
Charoensri et al. "An optimized expression vector for improving the yield of dengue virus-like particles from transfected insect cells" Journal of Virological Methods, vol. 205, 2014 (pp. 116-123).
Cox et al. "Predicting Zika virus structural biology: Challenges and opportunities for intervention" Antiviral Chemistry and Chemotherapy, vol. 24 (3-4), 2015 (pp. 118-126).
De Wispelaere Melissanne, et al., "Mutagenesis of the DI/DIII Linker in Dengue Virus Envelope Protein Impairs Viral Particle Assembly", Journal of Virology, 2012, vol. 86, No. 13, pp. 7072-7083, ISSN: 0022-538X, Abstract, Fig.1, Fig.8-9, p. 7073.
GenBank: AAB02517.1, "structural polyprotein precursor [Venezuelan equine encephalitis virus]", dated Nov. 17, 2004, retrieved from https://www.ncbi.nlm.nih.gov/protein/AAB02517.1 (2 pages).
GenBank: ADG95942.1, structural polyprotein [Chikungunya virus] http://www.ncbi.nlm.nih.gov/protein/296124572?report=genbank&log$=protalign&blast_rank=2&FiID=PBR7NTOU015. Dec. 28, 2010 (3 pages).
GenBank "Zika virus strain MR 766, complete genome" AY632535. 2, Nov. 23, 2010 (6 pages total) [Retrieved on May 16, 2017] Retrieved from the Internet, URL: https://www.ncbi.nlm.nih.gov/nuccore/AY632535 (6 pages).
Haddow A. D. et al., "Genetic Characterization of Zika Virus Strains: Geographic Expansion of the Asian Lineage" PLOS Neglected Tropical Disease, Feb. 2012, vol. 6, Issue 2, e1477 (7 pages total).
Hsieh Szu-Chia, et al., "A strong endoplasmic reticulum retention signal in the stem-anchor region of envelope glycoprotein of dengue virus type 2 affects the production of virus-like particles", Virology, 2008, vol. 374, No. 2, pp. 338-350, ISSN: 0042-6822.
Hsieh Szu-Chia et al. "The length of and nonhydrophobic residues in the transmembrane domain of dengue virus envelope protein are critical for its retention and assembly in the endoplasmic reticulum" Journal of Virology, vol. 84 No. 9, Apr. 2010 (pp. 4782-4797).
WHO Dengue vaccine research, "Immunization, Vaccines and Biologicals", http://www.who.int/immunization/research/development/dengue_vaccines/en/ (total 3 pages).
Huang Claire Y.H., et al., "The dengue virus type 2 envelope protein fusion peptide is essential for membrane fusion", Virology, 2010, vol. 396, No. 2, pp. 305-315, ISSN:0042-6822, Table, Fig.5, pp. 310-313.
Khetarpal Niyati, et al., "Dengue-specific subviral nanoparticles: design, creation and characterization", Journal of Nanobiotechnology, 2013, vol. 11, No. 15, total 8 pages, ISSN: 1477-3155.
Kostyuchenko V et al., "Structure of the thermally stable Zika virus", Nature, May 19, 2016, vol. 533, pp. 425-428.
Larocca et al., "Vaccine Protection Against Zika Virus from Brazil", Nature, Aug. 25, 2016, 536(7617), 474-478, doi:10.1038/nature18952 (24 pages total).
Lin et al., "Analysis of Epitopes on Dengue Virus Envelope Protein Recognized by Monoclonal Antibodies and Polyclonal Human Sera by a High Throughput Assay", PLOS, Jan. 2012, 6(1):e1447, total 12 pages.
Purdy D et al., "Secretion of noninfectious dengue virus-like particles and identification of amino acids in the stem region involved in intracellular retention of envelope protein" Virology, 2005, vol. 333, No. 2, pp. 239-250, ISSN: 0042-6822, Abstract, Fig. 1-4. Table 1, pp. 240, 247-248.

(56) References Cited

OTHER PUBLICATIONS

Richner et al. "Modified mRNA vaccines protect against Zika Virus infection" Cell, vol. 168., Mar. 9, 2017 , pp. 1114-1125, (23 pages total).
Seligman S, "Constancy and diversity in the flavivirus fusion peptide", BioMed Central, Virology Journal 2008, Feb. 14, 2008, total 10 pages. URL: http://www.virologyj.com/content/5/1/27.
Taylor et al. "Production of immunogenic West Nile virus-like particles using a herpes simplex virus 1 recombinant vector" Virology, vol. 496, 2016 (pp. 186-193).
Tsai et al., "Complexity of Neutralizing Antibodies against Multiple Dengue Virus Serotypes after Heterotypic Immunization and Secondary Infection Revealed by In-Depth Analysis of Cross-Reactive Antibodies", Journal of Virology, Jul. 2015, vol. 89, No. 14, pp. 7348-7362.
Heinz F et al., "Flaviviruses and flavivirus vaccines", Vaccine 30 (2012) 4301-4306.
Yamaji et al. "Efficient production of Japanese encephalitis virus-like particles by recombinant lepidopteran insect cells" Appl. Microbiol Biotechnol, vol. 97, 2013 (pp. 1071-1079).
Zhang et al., "Vaccination with dengue virus-like particles induces humoral and cellular immune responses in mice", Virology Journal, 2011, 8:333, total 9 pages.
Zika virus fact sheet, updated Sep. 6, 2016; URL:http://www.who.int/mediacentre/factsheets/zika/en/ ( 5 pages total).
Urakami et al., "Development of a Novel Virus-Like Particle Vaccine Platform That Mimics the Immature Form of Alphavirus," Clinical and Vaccine Immunology, 24(7): e00090-17 (pp. 1-14).
Veltrop-Duits et al., "Human CD4+ T cells stimulated by conserved adenovirus 5 hexon peptides recognize cells infected with different species of human adenovirus", Eur. J. Immunol., 2006, vol. 36, pp. 2410-2423 (14 pages total).
Akane Urakami et al., "An Envelope-Modified Tetravalent Dengue Virus-Like-Particle Vaccine Has Implications for Flavivirus Vaccine Design", Journal of Virology, Dec. 2017, vol. 91, Issue 23, e01181-17 (16 pages total).
Palucha et al., "Virus-Like Particles: Models for Assembly Studies and Foreign Epitope Carriers," Progress in Nucleic Acid Research and Molecular Biology, 2005, vol. 30, pp. 135-168.
Veltrop-Duits et al., Human CD4+T cells stimulated by conserved adenovirus 5 hexon peptides recognize cells infected with different species of human adenovirus, Eur. J. Immunol. 2006, vol. 36, pp. 2410-2423.
Metz et al., PLoS ONE, 2011, vol. 6, Issue 10, pp. 1-10.
Liu et al., "Recombinant dengue virus-like particles from Pichia pastoris: efficient production and immunological properties," Vir. Genes, 2010: 40:53-59.
Berthet et al. GenBank: AHF49783.1; 2015 (3 pages).
Enfissi et al. GenBank: ALX35659.1, 2016 (3 pages).
Pushko, et al., Replicon-Helper Systems from Attenuated Venezuelan Encephalitis Virus: Expression of Heterologous Genes in Vitro and Immunization against Heterologous Pathogens in Vivo, Virology 239, 1997 (pp. 389-401).
Manjila, et al., "Novel gene delivery systems", International Journal of Pharmaceutical Investigation, vol. 3, Issue 1, Jan. 2013 (7 pages).
International Search Report and Written Opinion, dated Mar. 26, 2019, issued by the International Searching Authority in PCT/JP2018/046794.
Jose et al. "A Structural and functions perspective of alphavirus replication and assembly" Future Microbiol, 2009, vol. 4, No. 7, pp. 837-856.
Garmashova et al., "Analysis of Venezuelan Equine Encephalitis Virus Capsid Protein Function in the Inhibition of Cellular Transcription", Journal of Virology, Dec. 2007, pp. 13552-13565.
Taylor et al. "Mutation of the N-Terminal Region of Chikungunya Virus Capsid Protein: Implications for Vaccine Design", Feb. 21, 2017, vol. 8(1), pp. e01970-16.
Non-Final Office Action issued Oct. 2, 2019 in U.S. Appl. No. 16/225,181.
Final Office Action issued Apr. 29, 2020 in U.S. Appl. No. 16/225,181.
Advisory Action issued Sep. 9, 2020 in U.S. Appl. No. 16/225,181.
Non-Final Office Action issued Oct. 16, 2020 in U.S. Appl. No. 16/225,181.
Final Office Action issued Mar. 22, 2021 in U.S. Appl. No. 16/225,181.
Kevin C. Conlon et. al, "Cytokines in the Treatment of Cancer", Journal of Interferon & Cytokine Research, vol. 39, No. 1, 2019, pp. 6-21.
Pan, W. Y. et al., "Cancer Immunotherapy Using a Membrane-bound Interleukin-12 With B7-1 Transmembrane and Cytoplasmic Domains", Mol. Ther., 2012, vol. 20, No. 5, pp. 927-937.
Osada et al., "Co-delivery of antigen and IL-12 by Venezuelan equine encephalitis virus replicon particles enhances antigen-specific immune responses and antitumor effects", Cancer Immunol Immunother, 2012 vol. 61, pp. 1941-1951.

* cited by examiner

ALPHAVIRUS REPLICON VECTOR AND IMMUNOTHERAPY BY ADMINISTERING SAME

CROSS REFERENCE TO RELATED APPLICATIONS

This application claims the benefit of U.S. Provisional Patent Application No. 63/017,993 filed on Apr. 30, 2020. The entire disclosure of this prior application is hereby incorporated by reference.

TECHNICAL FIELD

The present disclosure relates generally to the field of a cytokine immunotherapy against cancer and/or inflammatory disease, specifically to an alphavirus replicon vector comprising a cytokine which is useful for the treatment of a cancer and/or an inflammatory disease.

BACKGROUND ART

Cytokines are molecular messengers of the innate and adaptive immunity that enable cells of the immune system to communicate over short distances, and play critical roles in regulating all aspects of immune responses, including lymphoid development, homeostasis, differentiation, tolerance and memory. Considering the ability of the immune system to recognize and destroy cancer cells, there has been considerable interest over the past decades in harnessing cytokines for the treatment of cancer.

Preclinical experiments with interferon alpha (IFNa), granulocyte-macrophage colony stimulating factor (GM-CSF), interleukin (IL)-2, IL-12, IL-15, and IL-21 have shown efficacy in multiple murine cancer models.

IFNa was the first cytokine approved for the treatment of human cancer, hairy cell leukemia (HCL) in 1986, and after evaluating many treatment regimens, high-dose IL-2 (HDIL-2) was approved for the treatment of metastatic renal cell carcinoma (mRCC) in 1992, and metastatic melanoma (MM) in 1998. Since the initial approval, IFNa has added indications for follicular lymphoma, adjuvant melanoma, mRCC combined with bevacizumab, and AIDS-related Kaposi's sarcoma. Nevertheless, cytokines as monotherapy have not fulfilled the initial excitement they induced.

Strategies to address the issue of local versus systemic effects have included local or cavitary cytokine administration and transduction of stimulating or effector cells with genes encoding the cytokine through plasmid or viral delivery to augment the modest success with cytokine monotherapy. Other new approaches include structure-based cytokine engineering to generate "superkines" with increased binding affinity for select receptors to increase antitumor responses and proportionately decrease stimulation of Tregs. The development of chimeric antibody-cytokine fusion proteins and infusion of anticytokines in association with cytokines improve their tumor localization and pharmacokinetics compared to the native molecule. Additional clinical investigations combine cytokines with anticancer vaccines, checkpoint inhibitor (CPI) antibodies (anti-CTLA-4 or anti-PD-1/PD-L1), and the injection of cytokines with cancer-directed monoclonal antibodies to increase the antibody-dependent cellular cytotoxicity (ADCC) of these antibodies, thereby augmenting their antitumor efficacy (Non Patent literature 1: Kevin C. Conlon et. al, JOURNAL OF INTERFERON & CYTOKINE RESEARCH Volume 39, Number 1, 2019, the contents of the document is herein incorporated by reference).

IL-12 is a 70 kDa heterodimeric cytokine comprised of two disulfide-linked proteins, IL-12A p35 (35 kDa) and IL-12B p40 (40 kDa), naturally produced by dendritic cells, macrophages, neutrophils, and human B-lymphoblastoid cells (NC-37) and is essential for the initiation of effective immune response.

IL-12 has emerged as one of the most potent agents for anticancer immunotherapy. Local IL-12 expression consistently appears to be one of the most effective methods to overcome the immune suppression due to its central role in T- and NK-cell-mediated inflammatory responses. However, clinical application of IL-12-based therapies remains problematic due to the potential lethal toxicity associated with systemic administration.

Oncolytic viruses encoding IL-12 have demonstrated strong anti-tumor effects in preclinical models of cancers (Non-Patent Literature 2: Pan, W. Y. et al., Mol. Ther. 20(5), 927-937 (2012), the contents of this document are herein incorporated by reference), however, systemic accumulation of IL-12 after delivery by oncolytic viruses remains potentially lethal to patients. Inefficient transduction of tumor cells with carrier vectors currently limits the overall antitumor effect of this approach.

More promising drug-inducible IL-12 systems are expected to manage the IL-12 levels over long periods with reducing level of toxicity for the clinical use.

CITATION LIST

[Non Patent Literature 1]
  Kevin C. Conlon et. al, JOURNAL OF INTERFERON & CYTOKINE RESEARCH Volume 39, Number 1, 2019
[Non Patent Literature 2]
  Pan, W. Y. et al., Mol. Ther. 20(5), 927-937 (2012)

SUMMARY OF INVENTION

The present disclosure relates to an improved cytokine immunotherapy against cancer and/or inflammatory disease.

Specifically, the present disclosure relates to a novel immunologically-active alphavirus replicon vector comprising, a polynucleotide which encodes alphavirus non-structural proteins nsp1, nsp2, nsp3 and nsp4 and a polypeptide comprising a cytokine. The vector is useful for the treatment of cancer and/or inflammatory disease while minimizing toxicity.

In another aspect, the present disclosure provides a composition comprising the above discussed alphavirus replicon vector and a pharmaceutically acceptable carrier. The pharmaceutically acceptable carrier may be a delivery vehicle, wherein the vector is encapsulated in the delivery vehicle. In preferred embodiments, the delivery vehicle may be an alphavirus particle consisting of alphavirus structural proteins that may include capsid and/or envelope proteins. In another embodiment, the delivery vehicle may be lipid nanoparticles (LNP).

In another aspect, the present disclosure provides the above discussed alphavirus replicon vector or the composition for use in the treatment or immunization against cancer or inflammatory disease.

In another aspect, the present disclosure provides a use of the above discussed alphavirus replicon vector or the composition in the manufacture of a medicament for the treatment or immunization against cancer or inflammatory disease.

In another aspect, the present disclosure provides a method of treating and/or immunizing against cancer or inflammatory disease in a subject, which comprises administering an effective amount of the above discussed alphavirus replicon vector or composition to the subject in need thereof.

DESCRIPTION OF EMBODIMENTS

Figure 1:
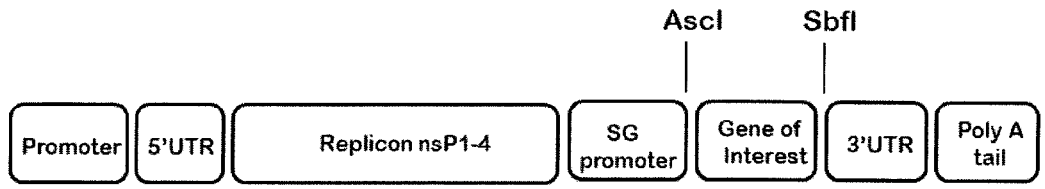
FIG. 1 A representative construct of an alphavirus replicon vector.

"Cytokine(s)" used herein is a polypeptide(s)/glycoprotein(s) derived from a natural lymphokine (cytokines made by lymphocytes), monokine (cytokines made by monocytes), chemokine (cytokines with chemotactic activities), an interleukin (cytokines made by one leukocyte and acting on other leukocytes), or modification thereof. The modified cytokine may be a fragment of the naturally occurring cytokine. In one embodiment, the modified cytokine has at least 70%, 75%, 80%, 85%, 90%, 95% or 98% amino acid sequence identity to a naturally occurring cytokine. In one embodiment, the modified cytokine is a mutant where at most 10% of the amino acids are deleted, substituted, and/or added based on a naturally occurring cytokine.

Examples of cytokines include, but are not limited to, interleukin (IL) including over 30 type such as IL-1α, IL-1β, IL-2, -3, -4, -5, -6, -7, -8, -9, -10, -11, -12, -13 to -37; interferon (IFN) such as IFN-α, IFN-5 β and IFN-γ; tumor necrosis factor (TNF) such as TNF-α and TNF-β; transforming growth factor (TGF) such as TGF-α and TGF-β; colony stimulating factor (CSF) such as granulocyte-colony stimulating factor (G-CSF), granulocyte-macrophage-colony 10 stimulating factor (GM-CSF), macrophage-colony Stimulating factor (M-CSF), erythropoietin (EPO), stem cell factor (SCF) and monocyte chemotactic and activating factor (MCAF); growth factor (GF) such as epidermal growth factor (EGF), fibroblast growth factor (FGF), insulin like growth 15 factor (IGF), nerve growth factor (NGF), Brain-derived neurotrophic factor (BDNF), platelet derived growth factor (PDGF), vascular endothelial growth factor (VEGF), hepatocyte growth factor (HGF), keratinocyte growth factor (KGF), thrombopoietin (TPO), and bone morphogenic protein 20 (BMP); and other polypeptide factors including LIF, kit ligand (KL), MPO (Myeloperoxidase) and CRP (C-reactive protein); COX (Cyclooxygenase) such as COX-1, COX-2 and COX-3, NOS (Nitric oxide synthase) such as NOS-1, NOS-2 and NOS-3; and modified thereof.

Cytokines also includes chemokines which are cytokines that induce chemotaxis. There are two major classes of chemokines, CXC and CC. The CXC chemokines, such as neutrophil-activating protein-2 (NAP-2) and melanoma growth stimulatory activity 5 protein (MGSA) are chemotactic primarily for neutrophils and T lymphocytes, whereas the CC chemokines, such as RANTES, Macrophage inflammatory protein (MIP) including MIP-1α and MIP-1β, keratinocyte-derived chemokine (KC), the monocyte 10 chemotactic proteins (MCP-1, MCP-2, MCP-3, MCP-4, and MCP-5) and the eotaxins (-1 and -2) are chemotactic for, among other cell types, macrophages, T lymphocytes, eosinophils, neutrophils, dendritic cells, and basophils. There also exist the chemokines lymphotactin-1, lymphotactin-2 (both C15 chemokines), and fractalkine (a CX3C chemokine) that do not fall into either of the major chemokine subfamilies.

Preferable example of a cytokine is, but not limited to, IL-12.

In the alphavirus replicon vector of the present disclosure, the gene encoding a cytokine may be fused to a gene encoding a transmembrane domain. As used herein, "transmembrane domain (TM)" is a protein derived either from a natural or from a synthetic source. Where the source is natural, the domain in some aspects is derived from any membrane-bound or transmembrane protein. In one aspect, the membrane-bound or transmembrane protein is a protein heterologous to the cytokine. Examples of the membrane-bound or transmembrane proteins may include the alpha, beta or zeta chain of a T-cell receptor, CD28, CD3 epsilon, CD45, CD4, CD5, CDS, CD9, CD16, CD22, CD33, CD37, CD64, CD80, CD86, CD134, CD137, CD154; toll-like receptors (TLR) such as TLR1-TLR10 in human and TLR1-TLR9, TLR11-TLR13 in mouse; interleukin (IL) receptors such as IL-1-28 receptor, RANTES receptors (CCR1, CCR3, CCR5), MIP-1 receptor, PF4 receptor, M-CSF receptor and NAP-2 receptor belonging to GPCR chemokine receptor; hemagglutinin (HA).

Examples of transmembrane proteins may also include the followings:

5-Lipoxygenase-Activating Protein, ABC Transporters, ACBP, Amyloid beta (A4), Bcl-2 Inhibitors, BNIPs, CAAX protease, Cytochromes P450, E-NPPs, EPHA1, EPHA2, EPHA3, EPHA4, Fatty Acid Desaturases, Gamma secretase, Glucose transporter, Glycophorins, GPCR, HER2/ErbB2, HER3/ErbB3, HER4/ErbB4, HSD-11β, Hypoxia-induced Proteins, Immunoglobulins, Insulin receptor, Integrins, Ion channel, MAPEG, MFS, MinK Family, MPPs, Peptidase AD, Peptidase Family M48, Peptidase MA, Protein Jagged, Receptor-type Kinases, SNARE Complex, Sulfatases, TNF receptor, Transmembrane Proteins 14, Transporter, TROBP, VEGF receptors, Aldehyde Dehydrogenases, Ammonia and Urea transporters, FMN-linked Oxidoreductases, Leucine Rich Repeat (LRR)-Containing Transmembrane Proteins, Leukotriene C4 synthase, Lysosome-associated membrane glycoprotein, Major Intrinsic Protein (MIP)/FNT superfamily, Microsomal prostaglandin E synthase, N-(deoxy)ribosyltransferase-like Membrane Proteins, Neutral/alkaline Ceramidases, Oligosaccharyl Transferase, Pentameric Ligand-gated Ion Channels, Rhodopsin-like receptors and pumps, Single-helix ATPase Regulators, Squalene/phytoene Synthase, Stearoyl-CoA desaturase 1, Stannin (SNN) Membrane Proteins, T-cell Surface Glycoprotein CD3 Zeta Chain, Tetratricopeptide repeat (TPR) Alpha-Helical Repeat Proteins, Transmembrane Proteins with NAD(P)-binding Rossmann-fold Domains.

In addition, monotypic/peripheral proteins that attached to the lipid bilayer or other integral proteins and peptide may also be used as transmembrane proteins. Examples may include Alpha/Beta-Hydrolase, Annexins, Bet V1-Like Protein, C1 Domain-Containing Protein, C2 Domain-containing Protein, CoA-Dependent Acyltransferases, CRAL-TRIO Domain-Containing Protein, DNase I-like protein, Fibrinogen, FYVE/PHD Zinc Finger Protein, Galactose-Binding Domain-Like Protein, Glycolipid Transfer Protein, Immunoglobulin-Like Superfamily (E Set) Protein, Lipocalin, Lipoxygenase, PGBD superfamily, PH Domain-Like Protein, Phosphatidylinositol 3-/4-Kinase, PLC-like Phosphodiesterase, Phosphotyrosine Protein Phosphatases II, P-Loop Containing Nucleoside Triphosphate Hydrolase, Protein kinase superfamily, PX Domain-Containing Protein, Saposin, Synuclein and Transcriptional factor tubby.

The expression "transmembrane domain" used in the present disclosure includes at least transmembrane region(s) of the membrane-bound or transmembrane protein. In addition, the transmembrane domain may also include juxtamembrane domain (JMD) and/or cytoplasmic tail of the membrane-bound or transmembrane protein.

Alternatively the transmembrane domain in some embodiments is synthetic. In some aspects, the synthetic transmembrane domain comprises predominantly hydrophobic residues such as leucine and valine. There are also highly charged residues flanking the transmembrane domain (stop transport signals). There are also highly charged residues flanking the transmembrane domain (stop transport signals). In some aspects, a triplet of phenylalanine, tryptophan and valine will be found at each end of a synthetic transmembrane domain.

Preferable examples of transmembrane domain may be those derived from TLR4 (Toll-like receptor 4) and influenza virus hemagglutinin (HA). Specific examples may include a protein consisting of the flexible juxtamembrane region or flexible linker, the transmembrane domain and the cytoplasmic tail of Influenza virus hemagglutinin "HA (flexible-TM-Cyt)" and a protein consisting of TLR4 (Toll-like receptor 4).

By fusing the gene encoding a cytokine with gene encoding a transmembrane domain, especially with the influenza virus hemagglutinin transmembrane domain, the safety of the resulting alphavirus replicon vector will be improved while keeping the effect to induce immunological activities.

A cytokine polypeptide and a transmembrane domain may be directly or indirectly fused. In one embodiment, one or two linkers may intervene between them.

Also a cytokine polypeptide and a transmembrane domain can be truncated and replaced by short linkers. In some embodiments, a cytokine structural protein and a heterologous transmembrane domain include one or more peptide linkers.

An example of a short linker consists of from 2 to 25 amino acids (e.g. 2, 3, 4, 5 or 6 amino acids). Usually, it is from 2 to 15 amino acids in length, such as SG, GS, SGG, GGS SGSG and TRGGS. In certain circumstances, the linker can be only one, such as glycine (G), serine (S) and cysteine (C).

When a cytokine polypeptide is chemically conjugated to a heterologous transmembrane domain through a chemical cross-linker which is a chemical compound, the examples of the cross-linkers include, but are not limited to, SMPH, Sulfo-MBS, Sulfo-EMCS, Sulfo-GMBS, Sulfo-SIAB, Sulfo-SMPB, Sulfo-SMCC, SVSB and SIA.

IgG-derived substances can also be used as a linker. Examples of IgG-derived substances include IgG1 to IgG4 comprising (i) full (hinge-CH2CH3) (ii) half (hinge-CH3) and (iii) short (12aa hinge only). Preferable example is IgG4-CH3.

The construct may also comprise a signal sequence. As used herein, "signal sequence" (sometimes referred to as signal peptide, targeting signal, localization signal, localization sequence, transit peptide, leader sequence or leader peptide) is a polynucleotide or polypeptide, depending on the context. Signal sequence is from about 9 to 200 nucleotides or 3-70 amino acids in length that, optionally, is incorporated at the 5' or N-terminus of the coding region or the protein. Some signal sequences are cleaved from the protein, for example by a signal peptidase after the proteins are transported to the desired site.

The signal sequence may be of the target protein to be expressed by the alphavirus replicon.

As used herein "alphavirus" is meant to refer to RNA-containing viruses that belong to the Togaviridae family of viruses. Exemplary Togaviridae viruses include but are not limited to Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, Buggy Creek Virus and Ockelbo virus.

By "alphavirus structural protein" is meant a polypeptide or fragment thereof having at least about 80% amino acid sequence identity to a naturally occurring viral capsid or envelope protein. In one embodiment, the alphavirus structural protein has at least about 85%, 90%, 95% or greater amino acid sequence identity with Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, or Buggy Creek Virus. Wild type amino acid sequences of alphavirus structural proteins can be obtained from GenBank.

In specific embodiments, the alphavirus is a CHIKV, for example CHIKV strain 37997 or LR2006 OPY-1. In other embodiments, the alphavirus is a VEEV, for example VEEV strain TC-83.

By "alphavirus replicon" is meant an RNA molecule which can direct its own amplification in vivo in a target cell. The replicon encodes the polymerase(s) which catalyze RNA amplification (nsp1, nsp2, nsp3, nsp4) and contains cis RNA sequences required for replication which are recognized and utilized by the encoded polymerase(s). An alphavirus replicon typically contains the following ordered elements: 5' UTR, sequences which encode alphavirus nonstructural proteins (nsp1, nsp2, nsp3, nsp4), 3' UTR, and a poly A signal. An alphavirus replicon also contains one or more viral sub-genomic promoters directing the expression of the gene of interest. Those sequences may have one or more mutations taught in a prior art.

In this disclosure, "alphavirus replicon", "alphavirus replicon vector" and "replicon" are used to refer the same substance.

An alphavirus replicon provided by the present disclosure may have the construct shown in FIG. 1.

By "alphavirus replicon particle" (ARP) is meant an alphavirus replicon packaged with alphavirus structural proteins. ARP does not contain polynucleotide encoding any of the alphavirus structural proteins.

In this disclosure, "comprises," "comprising," "containing" and "having" and the like can have the meaning ascribed to them in U.S. patent law and can mean "includes", "including," and the like; "consisting essentially of or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide.

A fragment may contain 10, 20, 30, 40, 50, 60, 70, 80, 90, or 100, 200, 300, 400, 500, 600, 700, 800, 900, or 1000 nucleotides or amino acids.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e<"3> and e<"100> indicating a closely related sequence.

By "effective amount" is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

A satisfactory effect may be obtained by systemic administration, e.g. intramuscular administration, intertumoral administration, subcutaneous administration or intravenous administration 1-8 times at the amount of $10^3$-$10^{10}$ Infectious Unit (IU) or 0.01-500 μg per time, preferably $10^5$-$10^{10}$ IU or 0.1-100 μg per time, for example $10^7$-$10^9$ IU or 1-50 μg per one time. The alphavirus replicon vector may preferably be formulated in a vaccine composition suitable for administration in a conventional manner.

By "subject" is meant a mammal, including, but not limited to, a human or non-human mammal, such as a bovine, equine, canine, ovine, or feline.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Unless specifically stated or obvious from context, as used herein, the term "or" is understood to be inclusive.

Examples of cancer which may be treated include, but are not limited to, melanoma, renal cancer, prostate cancer, breast cancer, colon cancer and non-small cell lung cancer. Other examples of the cancer include, but are not limited to, include bone cancer, pancreatic cancer, skin cancer (e.g. melanoma), cancer of the head or neck, cutaneous or intraocular malignant melanoma, uterine cancer, ovarian cancer, rectal cancer, cancer of the anal region, stomach cancer, liver cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations thereof.

"Inflammatory disease" includes inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankylosing spondylitis, Reiter syndrome, reactive arthritis, psoriatic arthritis, juvenile idiopathic arthritis and enterophathis arthritis, enthesitis, hypersensitivity (including both airways hypersensitivity and dermal hypersensitivity) and allergies. Specific autoimmune diseases include autoimmune haematological disorders (including e.g. hemolytic anaemia, aplastic anaemia, pure red cell anaemia and idiopathic thrombocytopenia), systemic lupus erythematosus (SLE), lupus nephritis, inflammatory muscle diseases (dermatomyosytis), periodontitis, polychondritis, scleroderma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and irritable bowel syndrome), endocrine ophthalmopathy, Graves' disease, sarcoidosis, multiple sclerosis, systemic sclerosis, fibrotic diseases, primary biliary cirrhosis, juvenile diabetes (diabetes mellitus type I), uveitis, keratoconjunctivitis sicca and vernal keratoconjunctivitis, interstitial lung fibrosis, periprosthetic osteolysis, glomerulonephritis (with and without nephrotic syndrome, e.g. including idiopathic nephrotic syndrome or minimal change nephropathy), multiple myeloma other types of tumors, inflammatory disease of skin and cornea, myositis, loosening of bone implants, metabolic disorders, (such as obesity, atherosclerosis and other cardiovascular diseases including dilated cardiomyopathy, myocarditis, diabetes mellitus type II, and dyslipidemia), and autoimmune thyroid diseases (including Hashimoto thyroiditis), small and medium vessel primary vasculitis, large vessel vasculitides including giant cell arteritis, hidradenitis suppurativa, neuromyelitis optica, Sjögren's syndrome, Behcet's disease, atopic and contact dermatitis, bronchiolitis, inflammatory muscle diseases, autoimmune peripheral neurophaties, immunological renal, hepatic and thyroid diseases, inflammation and atherothrombosis, autoinflammatory fever syndromes, immunohematological disorders, and bullous diseases of the skin and mucous membranes. Anatomically, uveitis can be anterior, intermediate, posterior, or pan-uveitis. It can be chronic or acute. The etiology of uveitis can be autoimmune or non-infectious, infectious, associated with systemic disease, or a white-dot syndrome.

In any of the foregoing aspects, the method further comprises administering a second composition comprising a checkpoint inhibitor polypeptide or polynucleotide encoding the same, and an optional pharmaceutically acceptable carrier. In some aspects, the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab.

Unless specifically stated or obvious from context, as used herein, the terms "a", "an", and "the" are understood to be singular or plural.

The art will acknowledge that polynucleotide sequences described in the specification and claims will recite "T"s in a representative DNA sequence but where the sequence represents RNA, the "T"s would be substituted for "U"s.

Any compositions or methods provided herein can be combined with one or more of any of the other compositions and methods provided herein.

The term "vector" refers to the means by which a nucleic acid sequence can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Typically, the nucleic acid molecule to be expressed is "operably linked" to a promoter and/or enhancer, and is subject to transcription regulatory control by the promoter and/or enhancer.

In one embodiment, an RNA molecule such as an alphavirus replicon may be generated by conventional procedures known to the art from a template DNA sequence. In vitro transcription (IVT) methods permit template-directed synthesis of RNA molecules. IVT methods permit synthesis of large quantities of RNA transcript. Generally, IVT utilizes a DNA template comprising a promoter sequence upstream of a sequence of interest. The promoter sequence is most commonly of bacteriophage origin such as the T7, T3 or SP6 promoter sequence but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand. Kits for in vitro transcription such as T7 transcription kit (RiboMax™ Express Large Scale RNA production System, Promega (WI USA)).

The method of transfection and the choice of expression vehicle will depend on the host system selected. Transfection methods are described, e.g., in Ausubel et al. (supra); expression vehicles may be chosen from those provided, e.g., in Cloning Vectors: A Laboratory Manual (P. H. Pouwels et al., 1985, Supp. 1987) The references cited in this paragraph are herein incorporated by reference.

A variety of expression systems exist for the production of the constructs of the invention. Expression vectors useful for producing the constructs include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as alphavirus (e.g. Chikungunya Virus (CHIKV) and Venezuelan Equine Encephalitis Virus (VEEV)), baculoviruses, papova viruses, such as SV40, vaccinia viruses, adenoviruses, fowl pox viruses, pseudorabies viruses and retroviruses, and vectors derived from combinations thereof.

Constructs and/or alphavirus replicon vectors used herein comprise alphavirus polynucleotides that encode structural proteins, including envelope proteins or capsid protein as described herein. Also, constructs and/or vectors used herein comprise alphavirus polynucleotides that encode nonstructural proteins nsp1, nsp2, nsp3 and nsp4 and a gene of interest. Specific example of the construct or vector is that shown in FIG. 1.

The vector may be, for example, a phage, plasmid, viral, or retroviral vector. The constructs and/or vectors that comprise the nucleotides should be operatively linked to an appropriate promoter, such as the CMV promoter, phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan.

Recombinant constructs can be prepared and used to transfect, can express viral proteins, including those described herein, into eukaryotic cells and/or prokaryotic cells. Thus, in one embodiment, the present disclosure provides for host cells which comprise a vector (or vectors) that contain nucleic acids which encode alphavirus structural proteins, including capsid, E3, E2, 6K, and E1 or portions thereof, and a vector that comprises nucleic acids which encode alphavirus nsp1, nsp2, nsp3 and nsp4, and at least one of gene of interest encoding a cytokine under conditions which allow the formation of alphavirus replicon particles. The term "alphavirus replicon particles" refers to particles consisting of alphavirus structural proteins in which the alphavirus replicon vector comprising polynucleotide encoding alphavirus nonstructural proteins nsp1, nsp2, nsp3 and nsp4 and a polypeptide comprising a cytokine is incorporated.

In one embodiment, said vector is a recombinant baculovirus.

In another embodiment, said recombinant baculovirus is transfected into an insect cell. In a preferred embodiment, said cell is an insect cell. In another embodiment, said insect cell is a Sf9 cell.

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved by using host strains that express T7 RNA polymerase in response to IPTG induction. Once produced, a recombinant polypeptide is then isolated according to standard methods known in the art, for example, those described herein.

Depending on the vectors and host cells selected, the constructs are produced by growing host cells transfected by the vectors under conditions whereby the recombinant proteins are expressed and the alphavirus replicon is generated, and constructs containing alphavirus replicon being packaged with the particle of alphavirus structural proteins are formed. In one embodiment, the invention comprises a method of producing a construct, that involves co-transfecting a vector comprising a polynucleotide encoding alphavirus non-structural protein nsp1, nsp2, nsp3 and nsp4, and at least one gene of interest encoding the polypeptide comprising a cytokine, at least one vector each encoding at least one alphavirus structural protein into suitable host cells and expressing said alphavirus structural protein under conditions that allow construct formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells that produce alphavirus replicon particles of the disclosure include, but are not limited to, batch, batch-fed, continuous and perfusion cell culture techniques. In one embodiment, cells co-transfected with a vector encoding an alphavirus replicon and a vector comprising a polypeptide encoding capsid, and a vector comprising a polynucleotide encoding envelope proteins, such as those derived from a CHIKV or VEEV are grown in a bioreactor or fermentation chamber where cells propagate and express protein (e.g., recombinant proteins) for purification and isolation. Typically, cell culture is performed under sterile, controlled temperature and atmospheric conditions. A bioreactor is a chamber used to culture cells in which environmental conditions such as temperature, atmosphere, agitation and/or pH can be monitored. In one embodiment, the bioreactor is a stainless steel chamber. In another embodiment, said bioreactor is a pre-sterilized plastic bag (e.g., Cellbag®, Wave Biotech, Bridgewater, N.J., the contents of the cited document is herein incorporated by reference). In other embodiment, said pre-sterilized plastic bags are about 50 L to 1000 L bags.

As used herein, the term "pharmaceutically acceptable carrier" means one or more compatible solid or liquid fillers, diluents or encapsulating substances which are suitable for administration to a human or other vertebrate animal, including any and all aqueous solvents (e.g., water, alcoholic/aqueous solutions, saline solutions, parenteral vehicles, such as sodium chloride, and Ringer's dextrose), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters. Encapsulating substances refers to a delivery vehicle where the polynucleotide or vector is packaged, such as a replicon particle (e.g. the alphavirus replicon particle described in US patent publication No. 2019-0185822, the contents of this document is herein incorporated by reference) and a lipid delivery system (e.g. liposome).

In some embodiments, the compositions or formulations of the present disclosure comprise a lipid delivery system, e.g., a liposome, a lioplexes, a lipid nanoparticle, or any combination thereof. The alphavirus replicon vector described herein can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that may primarily be composed of a lipid bilayer and may be used as a delivery vehicle for the administration of pharmaceutical formulations. Liposomes can be of different sizes. A multilamellar vesicle (MLV) may be hundreds of nanometers in diameter, and may contain a series of concentric bilayers separated by narrow aqueous compartments. A small unicellular vesicle (SUV) may be smaller than 50 nm in diameter, and a large unilamellar vesicle (LUV) may be between 50 and 500 nm in diameter. Liposome design may include, but is not limited to, opsonins or ligands to improve the attachment of liposomes to unhealthy tissue or to activate events such as, but not limited to, endocytosis. Liposomes may contain a low or a high pH value in order to improve the delivery of the pharmaceutical formulations.

The formation of liposomes may depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

In some embodiments, the alphavirus replicon vector described herein may be encapsulated by the liposome and/or it may be contained in an aqueous core that may then be encapsulated by the liposome.

In some embodiments, the alphavirus replicon vector described herein can be formulated in a cationic oil-in-water emulsion where the emulsion particle comprises an oil core and a cationic lipid that can interact with the polynucleotide anchoring the molecule to the emulsion particle. In some embodiments, the vector described herein can be formulated in a water-in-oil emulsion comprising a continuous hydrophobic phase in which the hydrophilic phase is dispersed.

In some embodiments, the alphavirus replicon vector described herein can be formulated in a lipid-polycation complex. As a non-limiting example, the polycation can include a cationic peptide or a polypeptide such as, but not limited to, polylysine, polyornithine and/or polyarginine and the cationic peptides.

In some embodiments, the alphavirus replicon vector described herein can be formulated in a lipid nanoparticle (LNP).

Lipid nanoparticle formulations typically comprise one or more lipids. In some embodiments, the lipid is a cationic or an ionizable lipid. In some embodiments, lipid nanoparticle formulations further comprise other components, including a phospholipid, a structural lipid, a quaternary amine compound, and a molecule capable of reducing particle aggregation, for example a PEG or PEG-modified lipid. In some embodiments, the amount of the cationic and ionizable lipids in the lipid composition ranges from about 0.01 mol % to about 99 mol %.

LNPs contain a pH-sensitive ionizable cationic lipid that attract anionic nucleic acids to form the core of self-assembling nanoparticle to ensure high encapsulation. At physiological pH, LNPs are neutral, eliminating a mechanism of toxicity seen with permanently cationic molecules.

These same pH-sensitive lipids are responsible for responding to the acidic environment of the endosome and triggering the disruption of the endosome and release of the nucleic acid into the cell.

This replicon based technology is a unique platform technology for the vaccination as a RNA can self-amplify to produce the vaccine antigen and deliver into the cellular organ. Moreover, this replicon based vaccine technology overcomes the challenges commonly associated with DNA based vaccines, such as risk of genome integration or the high doses and devices needed for administration, e.g. electroporation, and expects the higher immunogenicity with minimum dose based on the self-replication system over the mRNA technology.

According to the present disclosure, a novel immunologically-active alphavirus replicon vector which comprises a nucleic acid encoding a cytokine protein(s)/polypeptide(s), which is useful for the treatment of a cancer and/or an inflammatory disease while minimizing toxicity.

The invention will be described in detail with reference to the following examples, which, however, are not intended to limit the scope of the present application.

Example 1

Each gene encoding shown below constructs 1-6 was synthesized by Integrated DNA Technologies, Inc. (www.idtdna.com/pages).

Construct 1:

Gene encoding Mouse IL-12 sequence described below.

[Chem. 1]

| ssmIL-12B | mIL12-B (p40 w/o SS) | linker | mIL12A (p35 w/o SS) |

```
                                              (SEQ ID NO: 1)
MACPQKLTISWFAIVLLVSPLMAMWELEKDVYVVEVDWTPDAPGETVNLT

CDTPEEDDITWTSDQRHGVIGSGKTLTITVKEFLDAGQYTCHKGGETLSH

SHLLLHKKENGIWSTEILKNEKNKTFLKCEAPNYSGRFTCSWLVQRNMDL

KENIKSSSSPPDSRAVTCGMASLSAEKVTLDQRDYEKYSVSCQEDVTCPT

AEETLPIELALEARQQNKYENYSTSFFIRDIIKPDPPKNLQMKPLKNSQV

EVSWEYPDSWSTPHSYFSLKFFVRIQRKKEKMKETEEGCNQKGAFLVEKT

STEVQCKGGNVCVQAQDRYYNSSCSKWACVPCRVRSVPGVGVPGVGRVIP

VSGPARCLSQSRNLLKTTDDMVKTAREKLKHYSCTAEDIDHEDITRDQTS

TLKTCLPLELHKNESCLATRETSSTTRGSCLPPQKTSLMMTLCLGSIYED
```

-continued

LKMYQTEFQAINAALQNHNHQQIILDKGMLVAIDELMQSLNHNGETLRQK

PPVGEADPYRVKMKLCILLHAFSTRVVTINRVMGYLSSA

The linker is underlined.
Mouse IL-12B (p40)

(SEQ ID NO: 2)
MACPQKLTISWFAIVLLVSPLMAMWELEKDVYVVEVDWTPDAPGETVNLT

CDTPEEDDITWTSDQRHGVIGSGKTLTITVKEFLDAGQYTCHKGGETLSH

SHLLLHKKENGIWSTEILKNFKNKTFLKCEAPNYSGRFTCSWLVQRNMDL

KFNIKSSSSPPDSRAVTCGMASLSAEKVTLDQRDYEKYSVSCQEDVTCPT

AEEETLPIELALEARQQNKYENYSTSFFIRDIIKPDPPKNLQMKPLKNSQV

EVSWEYPDSWSTPHSYFSLKFFVRIQRKKEKMKETEEGCNQKGAFLVEKT

STEVQCKGGNVCVQAQDRYYNSSCSKWACVPCRVRS

Mouse IL-12A (35p) without Signal Sequence (SEQ ID NO: 3)
RVIPVSGPARCLSQSRNLLKTTDDMVKTAREKLKHYSCTAEDIDHEDITR

DQTSTLKTCLPLELHKNESCLATRETSSTTRGSCLPPQKTSLMMTLCLGS

IYEDLKMYQTEFQAINAALQNHNHQQIILDKGMLVAIDELMQSLNHNGET

LRQKPPVGEADPYRVKMKLCILLHAFSTRVVTINRVMGYLSSA

Linker (SEQ ID NO: 4)
VPGVGVPGVG

In the following constructs 2-6, "Mouse IL-12 (p40-p35)" corresponds to Construct 1.
Construct 2:
Gene encoding Mouse IL-12 (p40-p35) fused to human IgG4CH3 and HA (flexible domain-Transmembrane(TM)-Cytoplasmic Tail(Cyt)) with linkers.

[Chem. 2]

| Mouse IL-12 (p40-p35) | GS | Human IgG4CH3 | GS | HA (flex-TM-Cyt) |

(SEQ ID NO: 5)
MACPQKLTISWFAIVLLVSPLMAMWELEKDVYVVEVDWTPDAPGETVNLT

CDTPEEDDITWTSDQRHGVIGSGKTLTITVKEFLDAGQYTCHKGGETLSH

SHLLLHKKENGIWSTEILKNEKNKTELKCEAPNYSGRETCSWLVQRNMDL

KENIKSSSSPPDSRAVTCGMASLSAEKVTLDQRDYEKYSVSCQEDVTCPT

AEEETLPIELALEARQQNKYENYSTSFFIRDIIKPDPPKNLQMKPLKNSQV

EVSWEYPDSWSTPHSYFSLKFFVRIQRKKEKMKETEEGCNQKGAELVEKT

STEVQCKGGNVCVQAQDRYYNSSCSKWACVPCRVRSVPGVGVPGVGRVIP

VSGPARCLSQSRNLLKTTDDMVKTAREKLKHYSCTAEDIDHEDITRDQTS

TLKTCLPLELHKNESCLATRETSSTTRGSCLPPQKTSLMMTLCLGSIYED

LKMYQTEFQAINAALQNHNHQQIILDKGMLVAIDELMQSLNHNGETLRQK

PPVGEADPYRVKMKLCILLHAFSTRVVTINRVMGYLSSA<u>GS</u>GQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK<u>GS</u>

GVKLESMGIYQILAIYSTVASSLVLLVSLGAISFWMCSNGSLQCRICI

The underlined "GS" are linkers.
human IgG4 CH3:

(SEQ ID NO: 6)
GQPREPQVYTLPPSQEEMTKNQVSLTCLVKGFYPSDIAVEWESNGQPENN

YKTTPPVLDSDGSFELYSRLTVDKERWQEGNVESCSVMHEALHNHYTQKS

LSLSLGK

GS: linker (GGATCC)

HA(flexible-TM-Cyt):

(SEQ ID NO: 7)
GVKLESMGIYQILAIYSTVASSLVLLVSLGAISFWMCSNGSLQCRICI

Construct 3:
Gene encoding Mouse IL-12 (p40-p35) fused to HA (flexible-TM-Cyt) with a linker

[Chem. 3]

| Mouse IL-12 (p40-p35) | GS | HA (flex-TM-Cyt) |

(SEQ ID NO: 8)
MACPQKLTISWFAIVLLVSPLMAMWELEKDVYVVEVDWTPDAPGETVNLT

CDTPEEDDITWTSDQRHGVIGSGKILTITVKEFLDAGQYTCHKGGETLSH

SHLLLHKKENGIWSTEILKNEKNKTFLKCEAPNYSGRFTCSWLVQRNMDL

KENIKSSSSPPDSRAVTCGMASLSAEKVTLDQRDYEKYSVSCQEDVTCPT

AEEETLPIELALEARQQNKYENYSTSFFIRDIIKPDPPKNLQMKPLKNSQV

EVSWEYPDSWSTPHSYFSLKFFVRIQRKKEKMKETEEGCNQKGAFLVEKT

STEVQCKGGNVCVQAQDRYYNSSCSKWACVPCRVRSVPGVGVPGVGRVIP

VSGPARCLSQSRNLLKTTDDMVKTAREKLKHYSCTAEDIDHEDITRDQTS

TLKTCLPLELHKNESCLATRETSSTTRGSCLPPQKTSLMMTLCLGSIYED

LKMYQTEFQAINAALQNHNHQQIILDKGMLVAIDELMQSLNHNGETLRQK

-continued

PPVGEADPYRVKMKLCILLHAFSTRVVTINRVMGYLSSA<u>GS</u>GVKLESMGI

YQILAIYSTVASSLVLLVSLGAISFWMCSNGSLQCRICI

The underlined "GS" is a linker.

Construct 4:

Gene encoding mouse IL-12 (p40-p35) fused to human IgG4CH3 and human TLR4 (TM-Toll/interleukin-1 receptor domain (TIR)) with linkers

[Chem. 4]

| Mouse IL-12 (p40-p35) | GS | Human IgG4CH3 | GS | human TLR4(TM-TIR) |

(SEQ ID NO: 9)
MACPQKLTISWFAIVLLVSPLMAMWELEKDVYVVEVDWTPDAPGETVNLT

CDTPEEDDITWTSDQRHGVIGSGKTLTITVKEFLDAGQYTCHKGGETLSH

SHLLLHKKENGIWSTEILKNEKNKTFLKCEAPNYSGRETCSWLVQRNMDL

KENIKSSSSPPDSRAVTCGMASLSAEKVILDQRDYEKYSVSCQEDVTCPT

AEETLPIELALEARQQNKYENYSTSFFIRDIIKPDPPKNLQMKPLKNSQV

EVSWEYPDSWSTPHSYFSLKFFVRIQRKKEKMKETEEGCNQKGAFLVEKT

STEVQCKGGNVCVQAQDRYYNSSCSKWACVPCRVRSVPGVGVPGVGRVIP

VSGPARCLSQSRNLLKTTDDMVKTAREKLKHYSCTAEDIDHEDITRDQTS

TLKTCLPLELHKNESCLATRETSSTTRGSCLPPQKTSLMMTLCLGSIYED

LKMYQTEFQAINAALQNHNHQQIILDKGMLVAIDELMQSLNHNGETLRQK

PPVGEADPYRVKMKLCILLHAFSTRVVTINRVMGYLSSA<u>GS</u>GQPREPQVY

TLPPSQEEMTKNQVSLTCLVKGFYPSDIAVEWESNGQPENNYKTIPPVLD

SDGSFELYSRLTVDKSRWQEGNVESCSVMHEALHNHYTQKSLSLSLGK<u>GS</u>

KTIIGVSVLSVLVVSVVAVLVYKEYFHLMLLAGCIKYGRGENIYDAFVIY

SSQDEDWVRNELVKNLEEGVPPFQLCLHYRDFIPGVAIAANIIHEGFHKS

RKVIVVVSQHFIQSRWCIFEYEIAQTWQFLSSRAGIIFIVLQKVEKTLLR

QQVELYRLLSRNTYLEWEDSVLGRHIFWRRLRKALLDGKSWNPEGTVGTG

CNWQEATSI

The underlined "GS" are linkers.

human TLR4 (TM-TIR):

(SEQ ID NO: 10)
KTIIGVSVLSVLVVSVVAVLVYKFYFHLMLLAGCIK YGRGENIYDAFV

IYSSQDEDWVRNELVKNLEEGVPPFQLCLHYRDFIPGVAIAANIIHEGE

HKSRKVIVVVSQHFIQSRWCIFEYEIAQTWQFLSSRAGIIFIVLQKVEK

ILLRQQVELYRLLSRNTYLEWEDSVLGRHIFWRRLRKALLDGKSWNPEG

TVGTCNWQEATSI

Construct 5:

Gene encoding mouse IL-12 (p40-p35) fused to human TLR4 (TM-TIR) with linker

[Chem. 5]

| Mouse IL-12 (p40-p35) | GS | human TLR4(TM-TIR) |

(SEQ ID NO: 11)
MACPQKLTISWFAIVLLVSPLMAMWELEKDVYVVEVDWTPDAPGETVNL

TCDTPEEDDITWTSDQRHGVIGSGKTLTITVKEFLDAGQYTCHKGGETL

SHSHLLLHKKENGIWSTEILKNEKNKTFLKCEAPNYSGRETCSWLVQRN

MDLKENIKSSSSPPDSRAVTCGMASLSAEKVTLDQRDYEKYSVSCQEDV

TCPTAEETLPIELALEARQQNKYENYSTSFFIRDIIKPDPPKNLQMKPL

KNSQVEVSWEYPDSWSTPHSYFSLKFFVRIQRKKEKMKETEEGCNQKGA

FLVEKTSTEVQCKGGNVCVQAQDRYYNSSCSKWACVPCRVRSVPGVGVP

GVGRVIPVSGPARCLSQSRNLLKTTDDMVKTAREKLKHYSCTAEDIDHE

DITRDQTSTLKTCLPLELHKNESCLATRETSSTTRGSCLPPQKTSLMMT

LCLGSIYEDLKMYQTEFQAINAALQNHNHQQIILDKGMLVAIDELMQSL

NHNGETLRQKPPVGEADPYRVKMKLCILLHAFSTRVVTINRVMGYLSSA

<u>GS</u>KTIIGVSVLSVLVVSVVAVLVYKFYFHLMLLAGCIKYGRGENIYDAF

VIYSSQDEDWVRNELVKNLEEGVPPFQLCLHYRDFIPGVAIAANIIHEG

FHKSRKVIVVVSQHFIQSRWCIFEYEIAQTWQFLSSRAGIIFIVLQKVE

KTLLRQQVELYRLLSRNTYLEWEDSVLGRHIFWRRLRKALLDGKSWNPE

GTVGTGCNWQEATSI

The underlined "GS" is a linker.

Construct 6:

Gene encoding Mouse IL-12 (p40-p35) fused to Mouse IgG4CH3 and HA (flexible domain-Transmembrane(TM)-Cytoplasmic Tail(Cyt)) with linkers.

[Chem. 6]

| Mouse IL-12 (p40-p35) | GS | Mouse IgG4CH3 | GS | HA (flex-TM-Cyt) |

(SEQ ID NO: 12)
MACPQKLTISWFAIVLLVSPLMAMWELEKDVYVVEVDWTPDAPGETVNL

TCDTPEEDDITWTSDQRHGVIGSGKTLTITVKEFLDAGQYTCHKGGETL

SHSHLLLHKKENGIWSTEILKNFKNKTFLKCEAPNYSGRFTCSWLVQRN

MDLKFNIKSSSSPPDSRAVTCGMASLSAEKVTLDQRDYEKYSVSCQEDV

TCPTAEETLPIELALEARQQNKYENYSTSFFIRDIIKPDPPKNLQMKPL

KNSQVEVSWEYPDSWSTPHSYFSLKFFVRIQRKKEKMKETEEGCNQKGA

FLVEKTSTEVQCKGGNVCVQAQDRYYNSSCSKWACVPCRVRSVPGVGVP

GVGRVIPVSGPARCLSQSRNLLKTTDDMVKTAREKLKHYSCTAEDIDHE

DITRDQTSTLKTCLPLELHKNESCLATRETSSTTRGSCLPPQKTSLMMT

-continued

LCLGSIYEDLKMYQTEFQAINAALQNHNHQQIILDKGMLVAIDELMQSL

NHNGETLRQKPPVGEADPYRVKMKLCILLHAFSTRVVTINRVMGYLSSA

<u>GS</u>GRPKAPQVYTIPPPKEQMAKDKVSLTCMITNFFPEDITVEWQWNGQP

AENYKNTQPIMDTDGSYFVYSKLNVQKSNWEAGNTFTCSVLHEGLHNHH

TEKSLSHSPGK<u>GS</u>GVKLESMGIYQILAIYSTVASSLVLLVSLGAISFWM

CSNGSLQCRICI

The underlined "GS" are linkers.
Mouse IgG4CH3

(SEQ ID NO: 13)
GRPKAPQVYTIPPPKEQMAKDKVSLTCMITNFFPEDITVEWQWNGQPAE

NYKNTQPIMDTDGSYFVYSKLNVQKSNWEAGNTFTCSVLHEGLHNHHTE

KSLSHSPG

HA(flexible-TM-Cyt) and IgG4 are also disclosed as follows.
HA(flexible-TM-Cyt)
www.ncbi.nlm.nih.gov/protein/P03452
UniProtKB/Swiss-Prot: P03452.2
Human IgG4
www.uniprot.org/uniprot/P01861
UniProtKB: P01861

Example 2

Each gene encoding Construct 7 and 8 was prepared.
Construct 7:
Human IL-12 sequence described below.

[Chem. 7]

| SS hIL-12B | hIL-12B(p40 w/o SS) | Linker | hIL-12A(p35 w/o SS) |

(SEQ ID NO: 14)
<u>MCHQQLVISWFSLVFLASPLVAI</u>WELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVETDKT

SATVICRKNASISVRAQDRYYSSSWSEWASVPCS<u>VPGVGVPGVG</u>RNLPV

ATPDPGMFPCLHHSQNLLRAVSNMLQKARQTLEFYPCTSEEIDHEDITK

DKTSTVEACLPLELTKNESCLNSRETSFITNGSCLASRKTSFMMALCLS

SIYEDLKMYQVEFKTMNAKLLMDPKRQIFLDQNMLAVIDELMQALNFNS

ETVPQKSSLEEPDFYKTKIKLCILLHAFRIRAVTIDRVMSYLNAS

The first underline represents the signal sequence (SS) of human IL-12B (p40) and the second underline represents a linker.
Human IL-12B (p40)

(SEQ ID NO: 15)
<u>MCHQQLVISWFSLVFLASPLVAI</u>WELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCS

The underlined is the signal sequence (SS) of human IL-12B (p40).
Linker (Underline)

(SEQ ID NO: 4)
VPGVGVPGVG

Human IL-12A (p35) w/o Signal Sequence
(The signal sequence "MCPARSLLLVATLVLLDHLSLA (SEQ ID NO: 16)" is deleted)

(SEQ ID NO: 17)
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S

Construct 8:
Gene encoding human IL-12 (p40-p35) fused to human IgG4CH3 and HA (flexible domain-Transmembrane(TM)-Cytoplasmic Tail(Cyt)) with linkers.

[Chem. 8]

| Human IL-12 (p40-p35) | GS | Human IgG4CH3 | GS | HA (flex-TM-Cyt) |

In the above structure, "Human IL-12 (p40-p35)" corresponds to Construct 7.

(SEQ ID NO: 18)
MCHQQLVISWFSLVFLASPLVAIWELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVETDKT

SATVICRKNASISVRAQDRYYSSSWSEWASVPCSVPGVGVPGVGRNLPV

```
ATPDPGMFPCLHHSQNLLRAVSNMLQKARQTLEFYPCTSEEIDHEDITK

DKTSTVEACLPLELTKNESCLNSRETSFITNGSCLASRKTSFMMALCLS

SIYEDLKMYQVEFKTMNAKLLMDPKRQIFLDQNMLAVIDELMQALNFNS

ETVPQKSSLEEPDFYKTKIKLCILLHAFRIRAVTIDRVMSYLNASGSGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGKGSGVKLESMGIYQILAIYSTVASSLVLLVSLGAISFWMCSNG

SLQCRICI
```

The underlined "GS" are linkers.
Human IL-12B (p40)
UniProt: P29460
www.uniprot.org/uniprot/P29460
Human IL-12A (p35)
Uniprot: P29459
www.uniprot.org/uniprot/P29459

Example 3

Preparation of Vector

Schematic construct of the alphavirus replicon is shown in FIG. 1.

Figure 2:
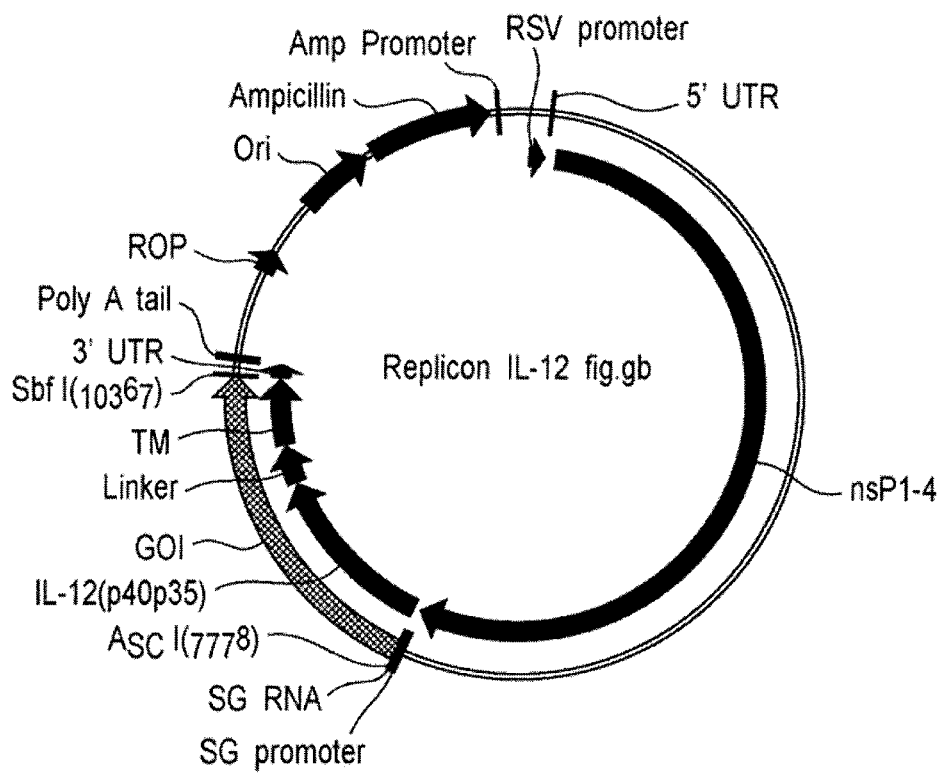
FIG. 2 Full length VEEV TC-83 vector of the construct including a polynucleotide encoding the construct comprising IL-12-Linker-TM produced in Example 3.

Each of constructs 1-6 prepared in Example 1 and constructs 7 and 8 prepared in Example 2 was used as gene of interest. Nucleotides encoding the construct was cloned into the VEEV replicon vector under the control of SG promoter. The VEEV replicon plasmid encoding each fragment was created by inserting AscI and SbfI restriction sites to obtain the full-length VEEV TC-83 replicon construct. See FIG. 2 for the construct with TM and FIG. 3 for the construct without TM.

Nucleotide sequences of SG promoter, 5'UTR, 3'UTR and Poly A tail are as follows. RNA sequences were obtained by using those DNA sequences as template.

SG promoter:

```
                                          (SEQ ID NO: 19)
cctgaatggactacgacatagtctagtccgccaag
```

5'UTR:

```
                                          (SEQ ID NO: 20)
ataggcggcgcatgagagaagcccagaccaattacctacccaaa
```

3'UTR:

```
                                          (SEQ ID NO: 21)
gcgatcgcatacagcagcaattggcaagctgcttacatagaactcgcgg cgattggcatgccgccttaaaattttttattttttattttctttttctttttc cgaatcggatttttgtttttaatatttc
```

Poly A tail:

```
                                          (SEQ ID NO: 22)
aaaaaaaaaaaaaaaaaaaaaaaaaaaaaaaaaaaaaaaaaaaaaaaaa
aaaaaa
```

VEEV TC-83 Replicon nsP1-4 amino acid sequence is as follows.

```
                                          (SEQ ID NO: 23)
MEKVHVDIEEDSPFLRALQRSFPQFEVEAKQVTDNDHANARAFSHLASK

LIETEVDPSDTILDIGSAPARRMYSKHKYHCICPMRCAEDPDRLYKYAT

KLKKNCKEITDKELDKKMKELAAVMSDPDLETETMCLHDDESCRYEGQV

AVYQDVYAVDGPTSLYHQANKGVRVAYWIGFDTTPFMFKNLAGAYPSYS

TNWADETVLTARNIGLCSSDVMERSRRGMSILRKKYLKPSNNVLFSVGS

TIYHEKRDLLRSWHLPSVFHLRGKQNYTCRCETIVSCDGYVVKRIAISP

GLYGKPSGYAATMHREGFLCCKVTDTLNGERVSFPVCTYVPATLCDQMT

GILATDVSADDAQKLLVGLNQRIVVNGRTQRNTNTMKNYLLPVVAQAFA

RWAKEYKEDQEDERPLGLRDRQLVMGCCWAFRRHKITSIYKRPDTQTII

KVNSDFHSFVLPRIGSNTLEIGLRTRIRKMLEEHKEPSPLITAEDIQEA

KCAADEAKEVREAEELRAALPPLAADFEEPTLEADVDLMLQEAGAGSVE

TPRGLIKVTSYAGEDKIGSYAVLSPQAVLKSEKLSCIHPLAEQVIVITH

SGRKGRYAVEPYHGKVVVPEGHAIPVQDFQALSESATIVYNEREFVNRY

LHHIATHGGALNTDEEYYKTVKPSEHDGEYLYDIDRKQCVKKELVTGLG

LTGELVDPPFHEFAYESLRTRPAAPYQVPTIGVYGVPGSGKSGIIKSAV

TKKDLVVSAKKENCAEIIRDVKKMKGLDVNARTVDSVLLNGCKHPVETL

YIDEAFACHAGTLRALIAIIRPKKAVLCGDPKQCGFFNMMCLKVHFNHE

ICTQVFHKSISRRCTKSVTSVVSTLFYDKRMRTTNPKETKIVIDTTGST

KPKQDDLILTCFRGWVKQLQIDYKGNEIMTAAASQGLTRKGVYAVRYKV

NENPLYAPTSEHVNVLLTRTEDRIVWKTLAGDPWIKILTAKYPGNFTAT

IEEWQAEHDAIMRHILERPDPTDVFQNKANVCWAKALVPVLKTAGIDMT

TEQWNTVDYFETDKAHSAEIVLNQLCVRETGLDLDSGLFSAPTVPLSIR

NNHWDNSPSPNMYGLNKEVVRQLSRRYPQLPRAVATGRVYDMNTGTLRN

YDPRINLVPVNRRLPHALVLHHNEHPQSDFSSFVSKLKGRTVLVVGEKL

SVPGKKVDWLSDQPEATFRARLDLGIPGDVPKYDIVFINVRTPYKYHHY

QQCEDHAIKLSMLTKKACLHLNPGGTCVSIGYGYADRASESIIGAIARQ

FKFSRVCKPKSSHEETEVLFVFIGYDRKARTHNPYKLSSTLTNIYTGSR

LHEAGCAPSYHVVRGDIATATEGVIINAANSKGQPGGGVCGALYKKFPE

SFDLQPIEVGKARLVKGAAKHIIHAVGPNFNKVSEVEGDKQLAEAYESI

AKIVNDNNYKSVAIPLLSTGIFSGNKDRLTQSLNHLLTALDTTDADVAI

YCRDKKWEMTLKEAVARREAVEEICISDDSSVTEPDAELVRVHPKSSLA

GRKGYSTSDGKTFSYLEGTKFHQAAKDIAEINAMWPVATEANEQVCMYI

LGESMSSIRSKCPVEESEASTPPSTLPCLCIHAMTPERVQRLKASRPEQ

ITVCSSFPLPKYRITGVQKIQCSQPILFSPKVPAYIHPRKYLVETPPVE

ETPESPAENQSTEGTPEQPALVNVDATRTRMPEPIIIEEEEEDSISLLS

DGPTHQVLQVEADIHGSPSVSSSSWSIPHASDFDVDSLSILDTLDGASV

TSGAVSAETNSYFARSMEFRARPVPAPRTVFRNPPHPAPRTRTPPLAHS

RASSRTSLVSTPPGVNRVITREELEALTPSRAPSRSASRTSLVSNPPGV
```

-continued

NRVITREEFEAFVAQQQXRFDAGAYIFSSDTGQGHLQQKSVRQTVLSEV

VLERTELEISYAPRLDQEKEELLRKKLQLNPTPANRSRYQSRRVENMKA

ITARRILQGLGHYLKAEGKVECYRTLHPVPLYSSSVNRAFSSPKVAVEA

CNAMLKENFPTVASYCIIPEYDAYLDMVDGASCCLDTASFCPAKLRSFP

KKHSYLEPTIRSAVPSAIQNTLQNVLAAATKRNCNVTQMRELPVLDSAA

FNVECFKKYACNNEYWETFKENPIRLTEENVVNYITKLKGPKAAALFAK

THNLNMLQDIPMDRFVMDLKRDVKVTPGTKHTEERPKVQVIQAADPLAT

ADLCGIHRELVRRLNAVLLPNIHTLFDMSAEDFDAIIAEHFQPGDCVLE

TDIASFDKSEDDAMALTALMILEDLGVDAELLTLIEAAFGEISSIHLPT

KTKFKFGAMMKSGMFLTLFVNTVINIVIASRVLRERLTGSPCAAFIGDD

NIVKGVKSDKLMADRCATWLNMEVKIIDAVVGEKAPYFCGGFILCDSVT

GTACRVADPLKRLFKLGKPLAVDDEHDDDRRRALHEESTRWNRVGILPE

LCKAVESRYETVGTSIIVMAMTTLASSVKSFSYLRGAPITLYG

Amino acid sequence corresponding to nsp3 is underlined.

In this example, amino acid sequence of nsp3 which is corresponding from 1330-1886 in SEQ ID NO: 23 was replaced with the sequence shown below. The underlined sequence was different from SEQ ID NO: 23.

(SEQ ID NO: 24)
APSYHVVRGDIATATEGVIINAANSKGQPGGGVCGALYKKFPESFDLQP

IEVGKARLVKGAAKHIIHAVGPNFNKVSEVEGDKQLAEAYESIAKIVND

NNYKSVAIPLLSTGIFSGNKDRLTQSLNHLLTALDTTDADVAIYCRDKK

WEMTLKEAVARREAVEEICISDDSSVTEPDAELVRVHPKSSLAGRKGYS

TSDGKTFSYLEGTKFHQAAKDIAEINAMWPVATEANEQVCMYILGKSMS

SIRSKCPVEESEASTPPSTLPCLCIHAMTPERVQRLKASRPEQITVCSS

FPLPKYRITGVQKIQCSQPILFSPKVPAYIHPRKYLVETPPVDETPEPS

AENQSTEGTPEQPPLITEDETRTRTPEPIIIEEEEEDSISLLSDGPTHQ

VLQVEADIHGPPSVSSSSWSIPHASDFDVDSLSILDTLEGASVTSGATS

AETNSYFAKSMEFLARPVPAPRTVFRNPPHPAPRTRTPSLAPSRACSRT

SLVSTPPGVNRVITREELEALTPSRTPSRSVSRTSLVSNPPGVNRVITR

EEFEAFVAQQQXRFDAGA

Example 4

Preparation of Alphavirus Replicon Particles (ARP)

10 μg of the full-length replicon plasmid for each of constructs 1-8 prepared in Example 3, 1 μg of VEEV Env expression plasmid and 1 μg of VEEV Capsid NLS mutant (or 1 μg VEEV Capsid expression plasmid) were transfected into HEK293T cells. The supernatant was harvested 48-96 hours after transfection. The replicon particles were purified by using an ion exchange column. The HEK293T or Vero cells was infected with the purified particles to determine the infectious titer. The purified replicon particles were used for the treatment of therapy.

Example 5

Effects of the Alphavirus Replicon Constructed to Express Construct 1

Figure 3:
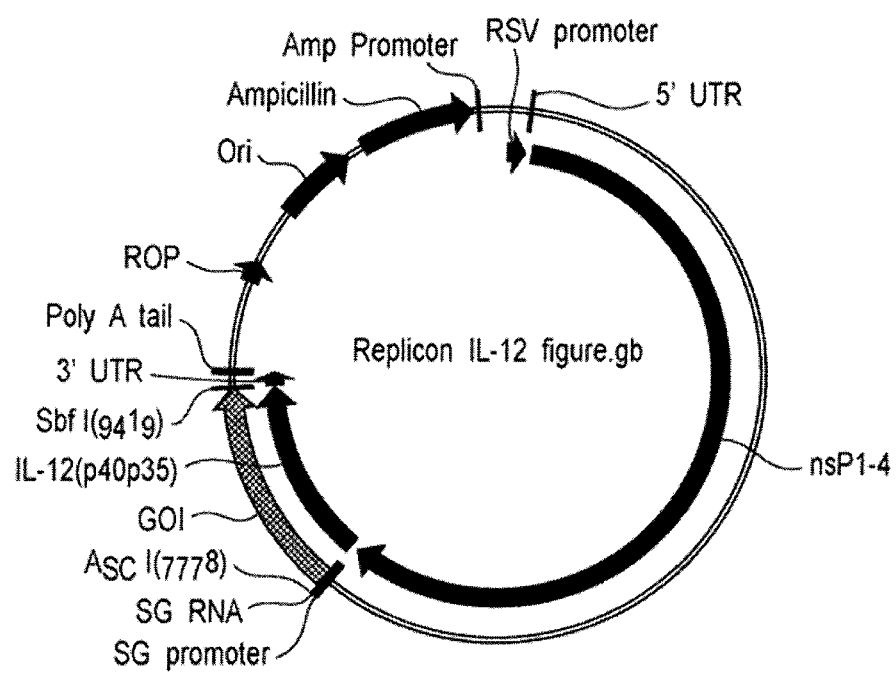
FIG. 3 Full length VEEV TC-83 vector of the construct including a polynucleotide encoding the construct comprising IL-12 produced in Example 3.

IL-12 alphavirus replicon particles prepared in Example 4 constructed to express construct 1 were evaluated. Mouse MC-38 subcutaneous syngeneic model was employed for the evaluation. MC-38 is a cell line derived from C57BL6 murine colon adenocarcinoma cells. C57BL/6 female mice (48 mice) were injected with $10^6$ cells, subcutaneously, into the rear flank. All mice were randomized into 6 groups (n=8 per group) when the average tumor volume reached 75-125 $mm^3$. Dosing was initiated within 24 hours of randomization (Day 0). Animals were dosed according to Table 1 below. The replicon Groups 3 and 4 assessed a control vector, constructed to express GFP as the gene of interest, and Groups 5 and 6 were constructed to express mouse IL-12 (Construct 1). The mice were injected with $1×10^9$ infectious unit dose (IU) of the indicated replicon intratumorally (i.t.) at one day intervals (total of 8 times) or with 10 mg/kg of anti-mouse PD-1 monoclonal antibody (clone RMP1-14, aPD-1 mAb) given by intraperitoneal injection (IP) biweekly for a total of 6 times. Animals were monitored, and tumors measured twice weekly for the duration of the study. The results are shown in FIG. 3. FIG. 3 shows mean and errors (s.e.m.) of tumor size in each group.

TABLE 1

| Group | Treatment | N | Dose Route | Dosing Frequency & Duration | Dose Level (mg/kg) | Dose Volume (mL/kg) |
|---|---|---|---|---|---|---|
| 1 | Vehicle (TNE buffer) | 8 | i.t. | 0, 2, 4, 6, 8, 10, 12, 14 | NA | 50 ul for each dose (Fixed volume) |
| 2 | aPD-1 mAb | 8 | IP | BIWX3 weeks (Total 6 dose) | 10 | 5 |
| 3 | Control ARP (GFP) | 8 | i.t. | 0, 2, 4, 6, 8, 10, 12, 14 | $10^9$ IU/dose | 50 ul for each dose (Fixed volume) |
| 4 | Control ARP (GFP) aPD-1 mAb | 8 8 | i.t. IP | 0, 2, 4, 6, 8, 10, 12, 14 BIWX3 weeks (Total 6 dose) | $10^9$ IU/dose 10 | 50 ul for each dose (Fixed volume) 5 |
| 5 | ARP mIL-12 | 8 | i.t. | 0, 2, 4, 6, 8, 10, 12, 14 | $10^9$ IU/dose | 50 ul for each dose (Fixed volume) |
| 6 | ARP mIL-12 aPD-1 mAb | 8 8 | i.t. IP | 0, 2, 4, 6, 8, 10, 12, 14 BIWX3 weeks (Total 6 dose) | $10^9$ IU/dose 10 | 50 ul for each dose (Fixed volume) 5 |

Figure 4:
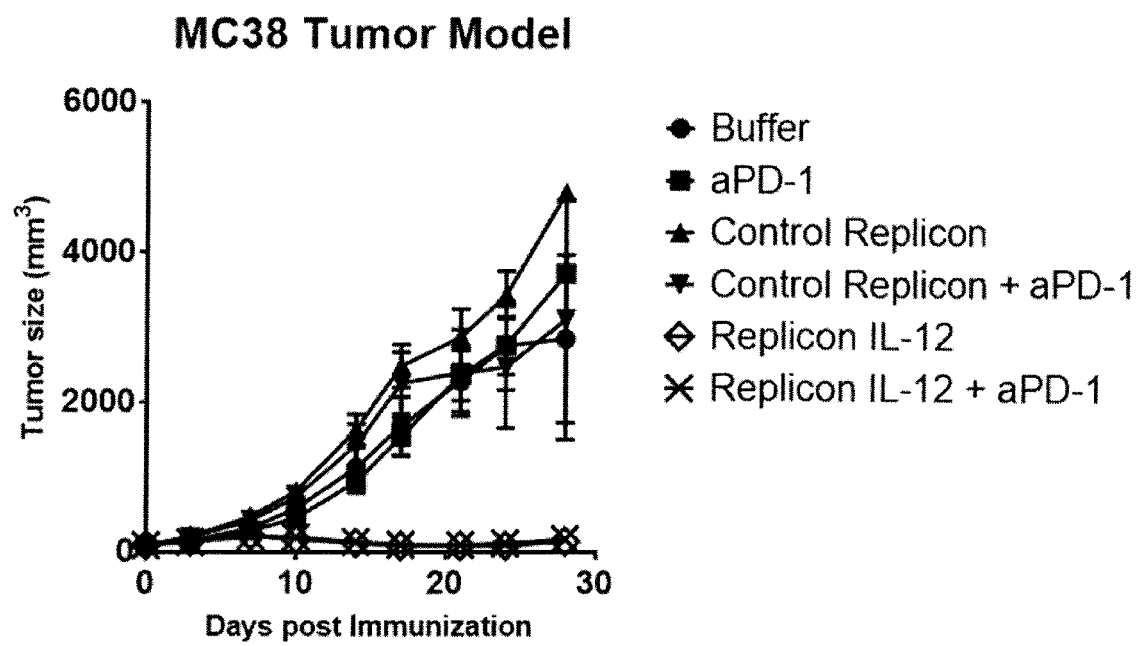
FIG. 4 Effect of IL-12 alphavirus replicon constructed to express construct 1 on MC-38 tumor model mice.

Results are shown in FIG. 4.

The data indicated that the IL-12 alphavirus replicon and the combination of IL-12 alphavirus replicon and anti-PD-1 antibody demonstrated superior anti-tumor effect over control and anti-PD-1 single immunotherapy.

Example 6

Effects of the Alphavirus Replicon Constructed to Express Construct 1

Figure 5:
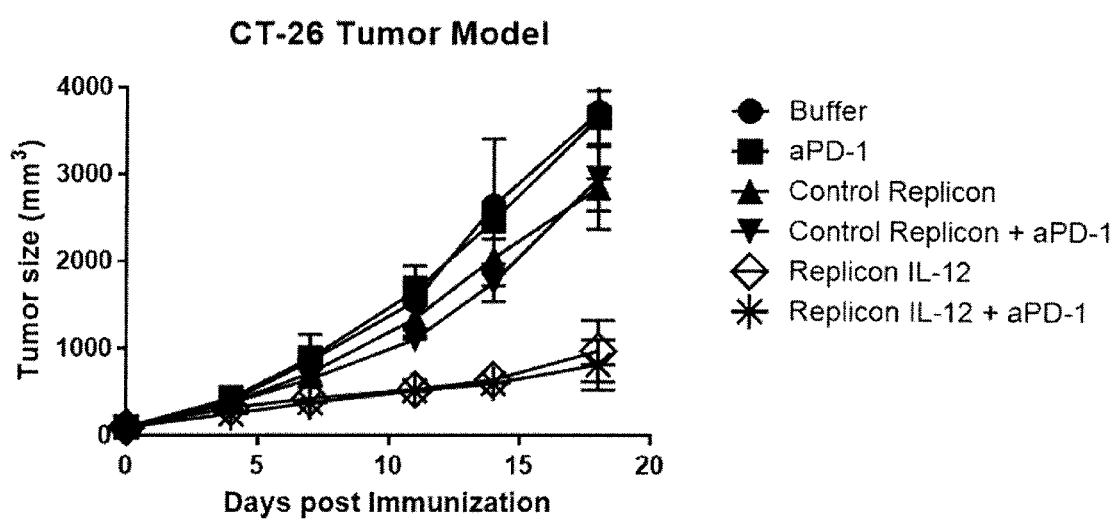
FIG. 5 Effect of IL-12 alphavirus replicon constructed to express construct 1 on CT-26 tumor model mice.

IL-12 alphavirus replicon particles (ARP) prepared in Example 4 constructed to express construct 1 were evaluated by using another cancer cell line. In this example, mouse CT-26 subcutaneous syngeneic mouse model was used. CT-26 is an N-nitroso-N-methylurethane-(NNMU) induced, undifferentiated colon carcinoma cell line. Balb/c female mice (48 mice) were injected with $5\times10^5$ cells subcutaneously into the rear flank. All mice were randomized into 6 groups (n=8 per group) when the average tumor volume reached 75-125 mm$^3$. Dosing was initiated within 24 hours of randomization (Day 0). Animals were dosed according to Table 2. The alphavirus replicon particles Group 3 and 4 were constructed to express GFP as a control vector and Groups 5 and 6 were constructed to express mouse IL-12 (Construct 1). The mice were injected with $4\times10^8$ infectious units (IU) of the indicated replicon intratumorally (i.t.) at one day intervals (total 8 injections) or with 10 mg/kg of an anti-mouse PD-1 monoclonal antibody (clone RMP1-14, aPD-1 mAb) given by intraperitoneal injection (IP), biweekly, for a total of 6 times. Animals were monitored and tumors were measured twice weekly for the duration of the study. The results are shown in FIG. 5. FIG. 5 shows mean and standard error of the mean (s.e.m.) of tumor size in each group.

TABLE 2

| Group | Treatment | N | Dose Route | Dosing Frequency & Duration | Dose Level (mg/kg) | Dose Volume (mL/kg) |
|---|---|---|---|---|---|---|
| 1 | Vehicle (TNE buffer) | 8 | i.t. | 0, 2, 4, 6, 8, 10, 12, 14 | NA | 50 ul for each dose (Fixed volume) |
| 2 | aPD-1 mAb | 8 | IP | BIWX3 weeks (Total 6 dose) | 10 | 5 |
| 3 | Control ARP (GFP) | 8 | i.t. | 0, 2, 4, 6, 8, 10, 12, 14 | $4 \times 10^8$ IU/dose | 50 ul for each dose (Fixed volume) |
| 4 | Control ARP (GFP) | 8 | i.t. | 0, 2, 4, 6, 8, 10, 12, 14 | $4 \times 10^8$ IU/dose | 50 ul for each dose (Fixed volume) |
|   | aPD-1 mAb | 8 | IP | BIWX3 weeks (Total 6 dose) | 10 | 5 |
| 5 | ARP IL-12 | 8 | i.t. | 0, 2, 4, 6, 8, 10, 12, 14 | $4 \times 10^8$ IU/dose | 50 ul for each dose (Fixed volume) |
| 6 | ARP IL-12 | 8 | i.t. | 0, 2, 4, 6, 8, 10, 12, 14 | $4 \times 10^8$ IU/dose | 50 ul for each dose (Fixed volume) |
|   | aPD-1 mAb | 8 | IP | BIWX3 weeks (Total 6 dose) | 10 | 5 |

The data indicated that IL-12 alphavirus replicon and the combination of IL-12 alphavirus replicon and anti-PD-1 antibody demonstrated superior anti-tumor effect over control and anti-PD-1 single immunotherapy.

Example 7

Effects of the Alphavirus Replicon Constructed to Express Construct 6

Figure 6A:
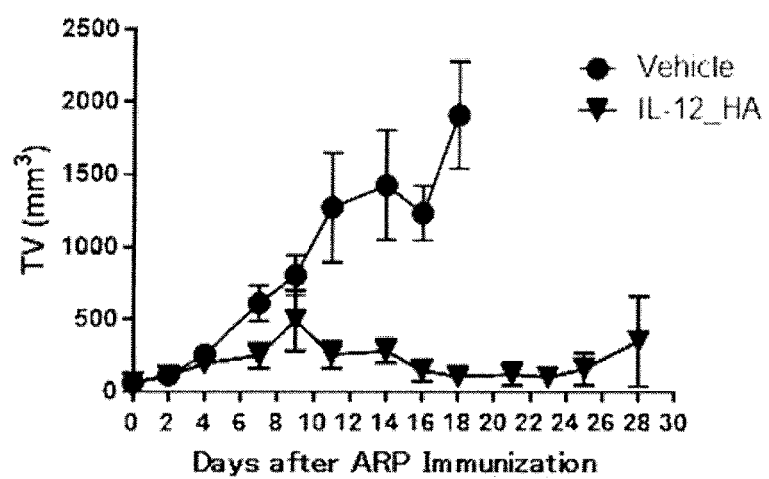
FIG. 6a Effect of IL-12 alphavirus replicon constructed to express construct 6 on CT-26 tumor model mice.
Figure 6B:
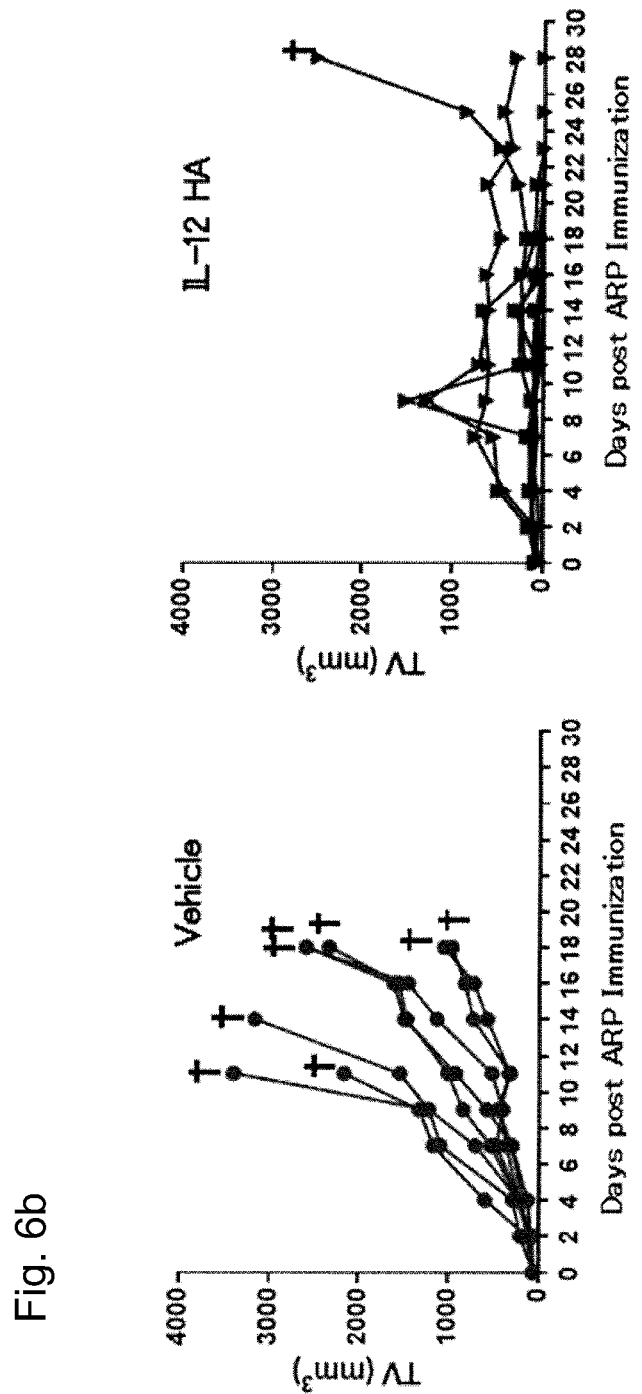
FIG. 6b Effect of IL-12 alphavirus replicon constructed to express construct 6 on CT-26 tumor model mice.

IL-12 alphavirus replicon particles prepared in Example 4 constructed to express construct 6 were evaluated. Balb/c female mice were injected with $1.75\times10^8$ CT-26 cells subcutaneously into the rear flank. All mice were randomized into 2 groups (n=8 per group) when the average tumor volume reached 50-100 mm$^3$. Dosing was initiated within 24 hours of randomization (Day 0). Animals were immunized with alphavirus replicon particles prepared in Example 4 expressing construct 6. The mice were injected with $4\times10^8$ infectious units (IU) of the indicated replicon intratumorally (i.t.) at one day intervals (total 8 injections). Animals were monitored and tumors were measured twice weekly for the duration of the study. The results are shown in FIG. 6a. FIG. 6a shows mean and standard error of the mean (s.e.m.) of tumor size in each group. FIG. 6b show tumor size of individual mouse (Left, vehicle, right, IL-12 HA). The cross symbols represent when each individual mouse was sacrificed due to large size of tumor.

The data indicates that IL-12 alphavirus replicon demonstrated potent anti-tumor effect.

Example 8

Effects of the Alphavirus Replicon Constructed to Express Construct 1

Figure 7A:
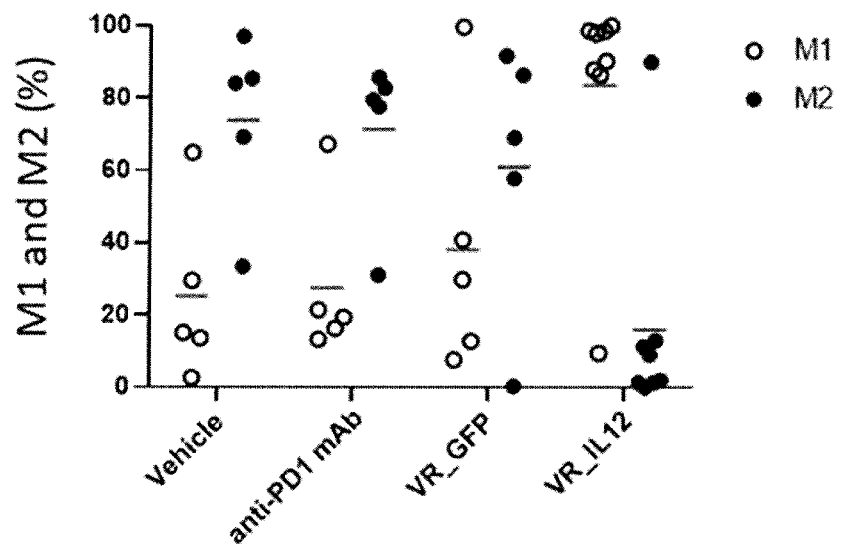
FIG. 7a Effect of IL-12 alphavirus replicon constructed to express construct 1 on macrophage M1 and M2 populations in TIL of MC-38 tumor model mice.
Figure 7B:
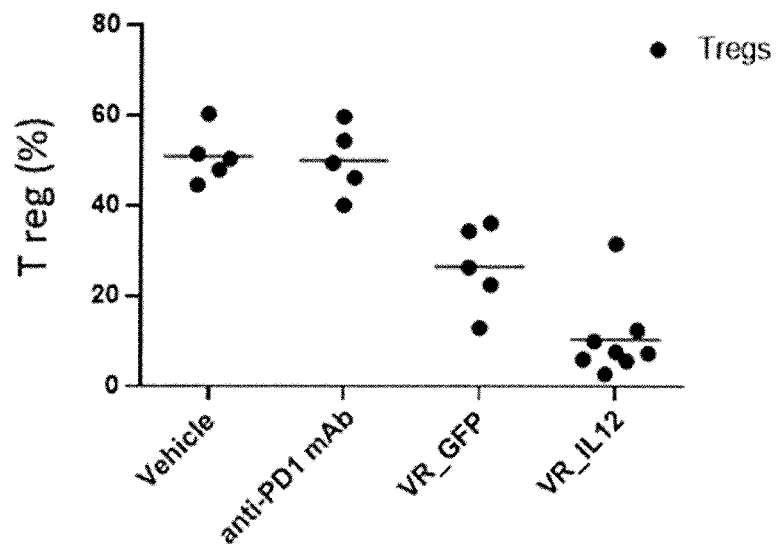
FIG. 7b Effect of IL-12 alphavirus replicon constructed to express construct 1 on Treg population in TIL of MC-38 tumor model mice.

IL-12 alphavirus replicon particles prepared in Example 4 constructed to express construct 1 were evaluated. C57BL6 female mice were injected with MC-38 cells subcutaneously into the rear flank. All mice were randomized into 4 groups (n=8 per group) when the average tumor volume reached 50-100 mm$^3$. Dosing was initiated within 24 hours of randomization (Day 0). The alphavirus replicon particles were constructed to express GFP as a control vector or to express mouse IL-12 (Construct 1). The mice were injected with $2.1\times10^8$ infectious units (IU) of the indicated replicon intratumorally (i.t.) at one day intervals (total 4 injections) on Day 0, 2, 4 and 6 or with 10 mg/kg of an anti-mouse PD-1 monoclonal antibody (clone RMP1-14, aPD-1 mAb) given by intraperitoneal injection (IP) on day 0 and 6. Animals were scarified on Day 9 and tumors collected and analyzed tumor-infiltrating lymphocytes (TIL) by FACS. The results are shown in FIG. 7. FIG. 7a shows M1 and M2 macrophage populations in macrophages contained in the TIL. Among the CD45$^+$CD11b$^+$F4/80$^+$ cells in the viable cells in TIL, M1 and M2 populations were identified by the markers of CD206 and IA/EA. FIG. 7b shows percentage of T regulatory cell (Treg) population in CD4$^+$T cells contained in the TIL. Among the CD45$^+$CD3$^+$CD4$^+$ cells in the TIL, the percentage of FoxP3$^+$ cells was determined as Treg population. The mice immunized with replicon expressing mouse IL-12 shows that 1) population of M1 macrophage was much higher compared to population of M2 macrophage and 2) the population of Treg cells in TIL was reduced.

Although not intended to be constrained by theory, the present inventor considers that the alphavirus replicon constructed to express IL-12 can provide potent anti-tumor effect by increasing the M1 macrophage population over the M2 macrophage and also by reducing the Treg population in the TIL, in addition to the other known effects exerted by IL-12.

Example 9

Effects of the Alphavirus Replicon Constructed to Express Construct 1

Figure 8:
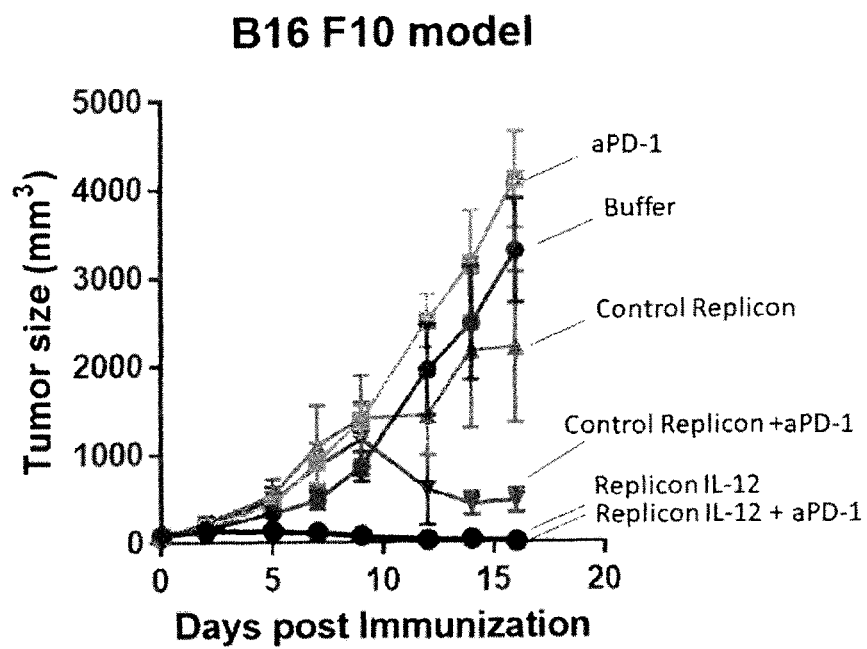
FIG. 8 Effect of IL-12 alphavirus replicon constructed to express construct 1 on B16F10 tumor model mice.

C57BL6 female mice were injected with B16F10 cells subcutaneously into the rear flank. All mice were randomized into 6 groups (n=8 per group) when the average tumor volume reached 50-100 mm³. B16F10 is a mouse cell line derived from melanoma. Dosing was initiated within 24 hours of randomization (Day 0). The alphavirus replicon particles were constructed to express GFP as a control vector or express mouse IL-12 (construct 1). The mice were injected with $1 \times 10^9$ infectious units (IU) of the indicated replicon intratumorally (i.t.) at one day intervals (total 8 injections) or with 10 mg/kg of an anti-mouse PD-1 monoclonal antibody (clone RMP1-14, aPD-1 mAb) given by intraperitoneal injection (IP) (total 6 injections). Animals were monitored and tumors were measured twice weekly for the duration of the study. The results are shown in FIG. 8. FIG. 8 shows mean and standard error of the mean (s.e.m.) of tumor size in each group.

The data indicated that IL-12 alphavirus replicon and the combination of IL-12 alphavirus replicon and anti-PD-1 antibody demonstrated superior anti-tumor effect over control and anti-PD-1 single immunotherapy.

What is claimed is:

1. A composition comprising (i) a pharmaceutically acceptable carrier, and (ii) an alphavirus replicon vector comprising a polynucleotide which encodes (i) alphavirus non-structural proteins nsp1, nsp2, nsp3 and nsp4, and (ii) a polypeptide comprising a cytokine, wherein the pharmaceutically acceptable carrier is a delivery vehicle and the alphavirus replicon vector is encapsulated in the delivery vehicle.

2. The alphavirus replicon vector of claim 1, wherein the cytokine is fused to a transmembrane domain.

3. The composition of claim 1, wherein the delivery vehicle is a particle consisting of alphavirus structural proteins or a lipid delivery system.

4. The composition of claim 3, wherein the alphavirus structural proteins comprise a capsid and at least one envelope proteins and the capsid has one or more alterations in the Nuclear Localization Signal (NLS).

5. The particle of claim 3, wherein the alphavirus structural proteins comprise at least one envelope protein E3 which comprises one or more alterations at the furin site in the E3 protein.

6. The composition according to claim 1, wherein the delivery vehicle is a lipid nanoparticle.

7. An alphavirus replicon vector comprising, a polynucleotide which encodes (i) alphavirus non-structural proteins nsp1, nsp2, nsp3 and nsp4, and (ii) a polypeptide comprising a cytokine, wherein the alphavirus is selected from the group consisting of CHIKV strain 37997, CHIKV strain OPY-1 and VEEV strain TC-83.

8. The alphavirus replicon vector of claim 7, wherein the cytokine is a lymphokine, monokine, chemokine, or interleukin.

9. The alphavirus replicon vector of claim 7, wherein the cytokine is an interleukin.

10. The alphavirus replicon vector of claim 9, wherein the interleukin is interleukin-12 (IL-12).

11. The alphavirus replicon vector of claim 7, which comprises a promoter, 5' UTR, polynucleotide encoding alphavirus non-structural proteins nsp1, nsp2, nsp3 and nsp4, SG promoter, a gene of interest encoding the polypeptide comprising a cytokine, 3'UTR and poly A tail.

12. The alphavirus replicon vector claim 7, wherein the polypeptide comprising a cytokine has the amino acid sequence of SEQ ID NO: 14 or 18.

13. A composition comprising (i) a pharmaceutically acceptable carrier, and (ii) an alphavirus replicon vector of claim 7.

14. The composition of claim 13, wherein the pharmaceutically acceptable carrier is a delivery vehicle and the alphavirus replicon vector is encapsulated in the delivery vehicle.

15. A composition comprising a lipid nanoparticle and the alphavirus replicon vector of claim 7, wherein the alphavirus replicon vector is encapsulated in the lipid nanoparticle.

16. A vaccine comprising the alphavirus replicon vector, according to claim 7.

17. A method of treating and/or immunizing against cancer or inflammatory disease in a subject, which comprises administering an effective amount of the alphavirus replicon vector of claim 7 to the subject in need thereof.

* * * * *

```
                        SEQUENCE LISTING

<160> NUMBER OF SEQ ID NOS: 24

<210> SEQ ID NO 1
   <211> LENGTH: 539
   <212> TYPE: PRT
   <213> ORGANISM: Artificial Sequence
   <220> FEATURE:
   <223> OTHER INFORMATION: Synthetic sequence, fused polypeptide
         comprising mouse IL-12B p40, linker and mouse IL-12A p35 without
         singal sequence (Mouse IL-12 (p40-p35))

<400> SEQUENCE: 1

Met Ala Cys Pro Gln Lys Leu Thr Ile Ser Trp Phe Ala Ile Val Leu
   1               5                   10                  15

Leu Val Ser Pro Leu Met Ala Met Trp Glu Leu Glu Lys Asp Val Tyr
                   20                  25                  30

Val Val Glu Val Asp Trp Thr Pro Asp Ala Pro Gly Glu Thr Val Asn
               35                  40                  45

Leu Thr Cys Asp Thr Pro Glu Glu Asp Ile Thr Trp Thr Ser Asp
           50                  55                  60

Gln Arg His Gly Val Ile Gly Ser Gly Lys Thr Leu Thr Ile Thr Val
   65                  70                  75                  80

Lys Glu Phe Leu Asp Ala Gly Gln Tyr Thr Cys His Lys Gly Gly Glu
                   85                  90                  95

Thr Leu Ser His Ser His Leu Leu Leu His Lys Lys Glu Asn Gly Ile
               100                 105                 110

Trp Ser Thr Glu Ile Leu Lys Asn Phe Lys Asn Lys Thr Phe Leu Lys
           115                 120                 125

Cys Glu Ala Pro Asn Tyr Ser Gly Arg Phe Thr Cys Ser Trp Leu Val
       130                 135                 140

Gln Arg Asn Met Asp Leu Lys Phe Asn Ile Lys Ser Ser Ser Ser Pro
   145                 150                 155                 160

Pro Asp Ser Arg Ala Val Thr Cys Gly Met Ala Ser Leu Ser Ala Glu
                   165                 170                 175

Lys Val Thr Leu Asp Gln Arg Asp Tyr Glu Lys Tyr Ser Val Ser Cys
               180                 185                 190

Gln Glu Asp Val Thr Cys Pro Thr Ala Glu Glu Thr Leu Pro Ile Glu
           195                 200                 205

Leu Ala Leu Glu Ala Arg Gln Gln Asn Lys Tyr Glu Asn Tyr Ser Thr
       210                 215                 220
```

```
Ser Phe Phe Ile Arg Asp Ile Ile Lys Pro Asp Pro Pro Lys Asn Leu
225                 230                 235                 240

Gln Met Lys Pro Leu Lys Asn Ser Gln Val Glu Val Ser Trp Glu Tyr
            245                 250                 255

Pro Asp Ser Trp Ser Thr Pro His Ser Tyr Phe Ser Leu Lys Phe Phe
        260                 265                 270

Val Arg Ile Gln Arg Lys Lys Glu Lys Met Lys Glu Thr Glu Glu Gly
    275                 280                 285

Cys Asn Gln Lys Gly Ala Phe Leu Val Glu Lys Thr Ser Thr Glu Val
290                 295                 300

Gln Cys Lys Gly Gly Asn Val Cys Val Gln Ala Gln Asp Arg Tyr Tyr
305                 310                 315                 320

Asn Ser Ser Cys Ser Lys Trp Ala Cys Val Pro Cys Arg Val Arg Ser
                325                 330                 335

Val Pro Gly Val Gly Val Pro Gly Val Gly Arg Val Ile Pro Val Ser
            340                 345                 350

Gly Pro Ala Arg Cys Leu Ser Gln Ser Arg Asn Leu Leu Lys Thr Thr
        355                 360                 365

Asp Asp Met Val Lys Thr Ala Arg Glu Lys Leu Lys His Tyr Ser Cys
    370                 375                 380

Thr Ala Glu Asp Ile Asp His Glu Asp Ile Thr Arg Asp Gln Thr Ser
385                 390                 395                 400

Thr Leu Lys Thr Cys Leu Pro Leu Glu Leu His Lys Asn Glu Ser Cys
                405                 410                 415

Leu Ala Thr Arg Glu Thr Ser Ser Thr Thr Arg Gly Ser Cys Leu Pro
            420                 425                 430

Pro Gln Lys Thr Ser Leu Met Met Thr Leu Cys Leu Gly Ser Ile Tyr
        435                 440                 445

Glu Asp Leu Lys Met Tyr Gln Thr Glu Phe Gln Ala Ile Asn Ala Ala
    450                 455                 460

Leu Gln Asn His Asn His Gln Gln Ile Ile Leu Asp Lys Gly Met Leu
465                 470                 475                 480

Val Ala Ile Asp Glu Leu Met Gln Ser Leu Asn His Asn Gly Glu Thr
                485                 490                 495

Leu Arg Gln Lys Pro Pro Val Gly Glu Ala Asp Pro Tyr Arg Val Lys
            500                 505                 510

Met Lys Leu Cys Ile Leu Leu His Ala Phe Ser Thr Arg Val Val Thr
        515                 520                 525

Ile Asn Arg Val Met Gly Tyr Leu Ser Ser Ala
    530                 535

<210> SEQ ID NO 2
<211> LENGTH: 336
<212> TYPE: PRT
<213> ORGANISM: Artificial Sequence
<220> FEATURE:
<223> OTHER INFORMATION: Synthetic sequence, mouse IL-12B (p40)

<400> SEQUENCE: 2

Met Ala Cys Pro Gln Lys Leu Thr Ile Ser Trp Phe Ala Ile Val Leu
1               5                   10                  15

Leu Val Ser Pro Leu Met Ala Met Trp Glu Leu Glu Lys Asp Val Tyr
            20                  25                  30

Val Val Glu Val Asp Trp Thr Pro Asp Ala Pro Gly Glu Thr Val Asn
        35                  40                  45
```

```
Leu Thr Cys Asp Thr Pro Glu Glu Asp Ile Thr Trp Thr Ser Asp
    50                  55                  60

Gln Arg His Gly Val Ile Gly Ser Gly Lys Thr Leu Thr Ile Thr Val
 65                  70                  75                  80

Lys Glu Phe Leu Asp Ala Gly Gln Tyr Thr Cys His Lys Gly Gly Glu
                 85                  90                  95

Thr Leu Ser His Ser His Leu Leu Leu His Lys Lys Glu Asn Gly Ile
            100                 105                 110

Trp Ser Thr Glu Ile Leu Lys Asn Phe Lys Asn Lys Thr Phe Leu Lys
            115                 120                 125

Cys Glu Ala Pro Asn Tyr Ser Gly Arg Phe Thr Cys Ser Trp Leu Val
130                 135                 140

Gln Arg Asn Met Asp Leu Lys Phe Asn Ile Lys Ser Ser Ser Ser Pro
145                 150                 155                 160

Pro Asp Ser Arg Ala Val Thr Cys Gly Met Ala Ser Leu Ser Ala Glu
                165                 170                 175

Lys Val Thr Leu Asp Gln Arg Asp Tyr Glu Lys Tyr Ser Val Ser Cys
            180                 185                 190

Gln Glu Asp Val Thr Cys Pro Thr Ala Glu Glu Thr Leu Pro Ile Glu
            195                 200                 205

Leu Ala Leu Glu Ala Arg Gln Gln Asn Lys Tyr Glu Asn Tyr Ser Thr
        210                 215                 220

Ser Phe Phe Ile Arg Asp Ile Ile Lys Pro Asp Pro Lys Asn Leu
225                 230                 235                 240

Gln Met Lys Pro Leu Lys Asn Ser Gln Val Glu Val Ser Trp Glu Tyr
                245                 250                 255

Pro Asp Ser Trp Ser Thr Pro His Ser Tyr Phe Ser Leu Lys Phe Phe
            260                 265                 270

Val Arg Ile Gln Arg Lys Lys Glu Lys Met Lys Glu Thr Glu Glu Gly
            275                 280                 285

Cys Asn Gln Lys Gly Ala Phe Leu Val Glu Lys Thr Ser Thr Glu Val
        290                 295                 300

Gln Cys Lys Gly Gly Asn Val Cys Val Gln Ala Gln Asp Arg Tyr Tyr
305                 310                 315                 320

Asn Ser Ser Cys Ser Lys Trp Ala Cys Val Pro Cys Arg Val Arg Ser
                325                 330                 335

<210> SEQ ID NO 3
<211> LENGTH: 193
<212> TYPE: PRT
<213> ORGANISM: Artificial Sequence
<220> FEATURE:
<223> OTHER INFORMATION: Synthetic sequence, mouse IL-12A (35p) without
      signal sequence

<400> SEQUENCE: 3

Arg Val Ile Pro Val Ser Gly Pro Ala Arg Cys Leu Ser Gln Ser Arg
 1               5                  10                  15

Asn Leu Leu Lys Thr Thr Asp Asp Met Val Lys Thr Ala Arg Glu Lys
                20                  25                  30

Leu Lys His Tyr Ser Cys Thr Ala Glu Asp Ile Asp His Glu Asp Ile
            35                  40                  45

Thr Arg Asp Gln Thr Ser Thr Leu Lys Thr Cys Leu Pro Leu Glu Leu
        50                  55                  60

His Lys Asn Glu Ser Cys Leu Ala Thr Arg Glu Thr Ser Ser Thr Thr
65                  70                  75                  80
```

```
Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala

<210> SEQ ID NO 4
<211> LENGTH: 10
<212> TYPE: PRT
<213> ORGANISM: Artificial Sequence
<220> FEATURE:
<223> OTHER INFORMATION: Synthetic sequence, linker

<400> SEQUENCE: 4

Val Pro Gly Val Gly Val Pro Gly Val Gly
1               5                   10

<210> SEQ ID NO 5
<211> LENGTH: 698
<212> TYPE: PRT
<213> ORGANISM: Artificial Sequence
<220> FEATURE:
<223> OTHER INFORMATION: Synthetic sequence, fused plypeptide comprising
      mouse IL-12(p40-p35), Human IgG4CH3 and Influenza HA(flex-TM-Cyt)

<400> SEQUENCE: 5

Met Ala Cys Pro Gln Lys Leu Thr Ile Ser Trp Phe Ala Ile Val Leu
1               5                   10                  15

Leu Val Ser Pro Leu Met Ala Met Trp Glu Leu Glu Lys Asp Val Tyr
                20                  25                  30

Val Val Glu Val Asp Trp Thr Pro Asp Ala Pro Gly Glu Thr Val Asn
            35                  40                  45

Leu Thr Cys Asp Thr Pro Glu Glu Asp Ile Thr Trp Thr Ser Asp
        50                  55                  60

Gln Arg His Gly Val Ile Gly Ser Gly Lys Thr Leu Thr Ile Thr Val
65                  70                  75                  80

Lys Glu Phe Leu Asp Ala Gly Gln Tyr Thr Cys His Lys Gly Gly Glu
                85                  90                  95

Thr Leu Ser His Ser His Leu Leu Leu His Lys Lys Glu Asn Gly Ile
            100                 105                 110

Trp Ser Thr Glu Ile Leu Lys Asn Phe Lys Asn Lys Thr Phe Leu Lys
        115                 120                 125

Cys Glu Ala Pro Asn Tyr Ser Gly Arg Phe Thr Cys Ser Trp Leu Val
    130                 135                 140

Gln Arg Asn Met Asp Leu Lys Phe Asn Ile Lys Ser Ser Ser Ser Pro
145                 150                 155                 160

Pro Asp Ser Arg Ala Val Thr Cys Gly Met Ala Ser Leu Ser Ala Glu
```

```
              165                 170                 175
Lys Val Thr Leu Asp Gln Arg Asp Tyr Glu Lys Tyr Ser Val Ser Cys
            180                 185                 190

Gln Glu Asp Val Thr Cys Pro Thr Ala Glu Glu Thr Leu Pro Ile Glu
            195                 200                 205

Leu Ala Leu Glu Ala Arg Gln Gln Asn Lys Tyr Glu Asn Tyr Ser Thr
            210                 215                 220

Ser Phe Phe Ile Arg Asp Ile Ile Lys Pro Asp Pro Pro Lys Asn Leu
225                 230                 235                 240

Gln Met Lys Pro Leu Lys Asn Ser Gln Val Glu Val Ser Trp Glu Tyr
            245                 250                 255

Pro Asp Ser Trp Ser Thr Pro His Ser Tyr Phe Ser Leu Lys Phe Phe
            260                 265                 270

Val Arg Ile Gln Arg Lys Lys Glu Lys Met Lys Glu Thr Glu Glu Gly
            275                 280                 285

Cys Asn Gln Lys Gly Ala Phe Leu Val Glu Lys Thr Ser Thr Glu Val
            290                 295                 300

Gln Cys Lys Gly Gly Asn Val Cys Val Gln Ala Gln Asp Arg Tyr Tyr
305                 310                 315                 320

Asn Ser Ser Cys Ser Lys Trp Ala Cys Val Pro Cys Arg Val Arg Ser
                325                 330                 335

Val Pro Gly Val Gly Val Pro Gly Val Gly Arg Val Ile Pro Val Ser
            340                 345                 350

Gly Pro Ala Arg Cys Leu Ser Gln Ser Arg Asn Leu Leu Lys Thr Thr
            355                 360                 365

Asp Asp Met Val Lys Thr Ala Arg Glu Lys Leu Lys His Tyr Ser Cys
370                 375                 380

Thr Ala Glu Asp Ile Asp His Glu Asp Ile Thr Arg Asp Gln Thr Ser
385                 390                 395                 400

Thr Leu Lys Thr Cys Leu Pro Leu Glu Leu His Lys Asn Glu Ser Cys
                405                 410                 415

Leu Ala Thr Arg Glu Thr Ser Ser Thr Thr Arg Gly Ser Cys Leu Pro
            420                 425                 430

Pro Gln Lys Thr Ser Leu Met Met Thr Leu Cys Leu Gly Ser Ile Tyr
            435                 440                 445

Glu Asp Leu Lys Met Tyr Gln Thr Glu Phe Gln Ala Ile Asn Ala Ala
            450                 455                 460

Leu Gln Asn His Asn His Gln Gln Ile Ile Leu Asp Lys Gly Met Leu
465                 470                 475                 480

Val Ala Ile Asp Glu Leu Met Gln Ser Leu Asn His Asn Gly Glu Thr
                485                 490                 495

Leu Arg Gln Lys Pro Pro Val Gly Glu Ala Asp Pro Tyr Arg Val Lys
            500                 505                 510

Met Lys Leu Cys Ile Leu Leu His Ala Phe Ser Thr Arg Val Val Thr
            515                 520                 525

Ile Asn Arg Val Met Gly Tyr Leu Ser Ser Ala Gly Ser Gly Gln Pro
            530                 535                 540

Arg Glu Pro Gln Val Tyr Thr Leu Pro Pro Ser Gln Glu Glu Met Thr
545                 550                 555                 560

Lys Asn Gln Val Ser Leu Thr Cys Leu Val Lys Gly Phe Tyr Pro Ser
                565                 570                 575

Asp Ile Ala Val Glu Trp Glu Ser Asn Gly Gln Pro Glu Asn Asn Tyr
            580                 585                 590
```

```
Lys Thr Thr Pro Pro Val Leu Asp Ser Asp Gly Ser Phe Phe Leu Tyr
        595                 600                 605

Ser Arg Leu Thr Val Asp Lys Ser Arg Trp Gln Glu Gly Asn Val Phe
    610                 615                 620

Ser Cys Ser Val Met His Glu Ala Leu His Asn His Tyr Thr Gln Lys
625                 630                 635                 640

Ser Leu Ser Leu Ser Leu Gly Lys Gly Ser Gly Val Lys Leu Glu Ser
            645                 650                 655

Met Gly Ile Tyr Gln Ile Leu Ala Ile Tyr Ser Thr Val Ala Ser Ser
        660                 665                 670

Leu Val Leu Val Ser Leu Gly Ala Ile Ser Phe Trp Met Cys Ser
            675                 680                 685

Asn Gly Ser Leu Gln Cys Arg Ile Cys Ile
        690                 695

<210> SEQ ID NO 6
<211> LENGTH: 107
<212> TYPE: PRT
<213> ORGANISM: Artificial Sequence
<220> FEATURE:
<223> OTHER INFORMATION: Synthetic sequence, human IgG4CH3

<400> SEQUENCE: 6

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 7
<211> LENGTH: 48
<212> TYPE: PRT
<213> ORGANISM: Artificial Sequence
<220> FEATURE:
<223> OTHER INFORMATION: Synthetic sequence, influenza HA(flexible-TM-
      Cyt)

<400> SEQUENCE: 7

Gly Val Lys Leu Glu Ser Met Gly Ile Tyr Gln Ile Leu Ala Ile Tyr
1               5                   10                  15

Ser Thr Val Ala Ser Ser Leu Val Leu Val Ser Leu Gly Ala Ile
            20                  25                  30

Ser Phe Trp Met Cys Ser Asn Gly Ser Leu Gln Cys Arg Ile Cys Ile
        35                  40                  45

<210> SEQ ID NO 8
<211> LENGTH: 589
<212> TYPE: PRT
<213> ORGANISM: Artificial Sequence
<220> FEATURE:
```

<223> OTHER INFORMATION: Synthetic sequence, fused polypeptide
comprising mouse IL-12(p40-p35) and influenza HA(Flex-TM-Cyt)

<400> SEQUENCE: 8

```
Met Ala Cys Pro Gln Lys Leu Thr Ile Ser Trp Phe Ala Ile Val Leu
1               5                   10                  15

Leu Val Ser Pro Leu Met Ala Met Trp Glu Leu Glu Lys Asp Val Tyr
            20                  25                  30

Val Val Glu Val Asp Trp Thr Pro Asp Ala Pro Gly Glu Thr Val Asn
        35                  40                  45

Leu Thr Cys Asp Thr Pro Glu Glu Asp Ile Thr Trp Thr Ser Asp
    50                  55                  60

Gln Arg His Gly Val Ile Gly Ser Gly Lys Thr Leu Thr Ile Thr Val
65                  70                  75                  80

Lys Glu Phe Leu Asp Ala Gly Gln Tyr Thr Cys His Lys Gly Gly Glu
                85                  90                  95

Thr Leu Ser His Ser His Leu Leu Leu His Lys Lys Glu Asn Gly Ile
            100                 105                 110

Trp Ser Thr Glu Ile Leu Lys Asn Phe Lys Asn Lys Thr Phe Leu Lys
        115                 120                 125

Cys Glu Ala Pro Asn Tyr Ser Gly Arg Phe Thr Cys Ser Trp Leu Val
    130                 135                 140

Gln Arg Asn Met Asp Leu Lys Phe Asn Ile Lys Ser Ser Ser Ser Pro
145                 150                 155                 160

Pro Asp Ser Arg Ala Val Thr Cys Gly Met Ala Ser Leu Ser Ala Glu
                165                 170                 175

Lys Val Thr Leu Asp Gln Arg Asp Tyr Glu Lys Tyr Ser Val Ser Cys
            180                 185                 190

Gln Glu Asp Val Thr Cys Pro Thr Ala Glu Glu Thr Leu Pro Ile Glu
        195                 200                 205

Leu Ala Leu Glu Ala Arg Gln Gln Asn Lys Tyr Glu Asn Tyr Ser Thr
    210                 215                 220

Ser Phe Phe Ile Arg Asp Ile Ile Lys Pro Asp Pro Lys Asn Leu
225                 230                 235                 240

Gln Met Lys Pro Leu Lys Asn Ser Gln Val Glu Val Ser Trp Glu Tyr
                245                 250                 255

Pro Asp Ser Trp Ser Thr Pro His Ser Tyr Phe Ser Leu Lys Phe Phe
            260                 265                 270

Val Arg Ile Gln Arg Lys Lys Glu Lys Met Lys Glu Thr Glu Glu Gly
        275                 280                 285

Cys Asn Gln Lys Gly Ala Phe Leu Val Glu Lys Thr Ser Thr Glu Val
    290                 295                 300

Gln Cys Lys Gly Gly Asn Val Cys Val Gln Ala Gln Asp Arg Tyr Tyr
305                 310                 315                 320

Asn Ser Ser Cys Ser Lys Trp Ala Cys Val Pro Cys Arg Val Arg Ser
                325                 330                 335

Val Pro Gly Val Gly Val Pro Gly Val Gly Arg Val Ile Pro Val Ser
            340                 345                 350

Gly Pro Ala Arg Cys Leu Ser Gln Ser Arg Asn Leu Leu Lys Thr Thr
        355                 360                 365

Asp Asp Met Val Lys Thr Ala Arg Glu Lys Leu Lys His Tyr Ser Cys
    370                 375                 380

Thr Ala Glu Asp Ile Asp His Glu Asp Ile Thr Arg Asp Gln Thr Ser
385                 390                 395                 400
```

```
Thr Leu Lys Thr Cys Leu Pro Leu Glu Leu His Lys Asn Glu Ser Cys
            405                 410                 415

Leu Ala Thr Arg Glu Thr Ser Ser Thr Thr Arg Gly Ser Cys Leu Pro
        420                 425                 430

Pro Gln Lys Thr Ser Leu Met Met Thr Leu Cys Leu Gly Ser Ile Tyr
            435                 440                 445

Glu Asp Leu Lys Met Tyr Gln Thr Glu Phe Gln Ala Ile Asn Ala Ala
        450                 455                 460

Leu Gln Asn His Asn His Gln Gln Ile Ile Leu Asp Lys Gly Met Leu
465                 470                 475                 480

Val Ala Ile Asp Glu Leu Met Gln Ser Leu Asn His Asn Gly Glu Thr
                485                 490                 495

Leu Arg Gln Lys Pro Pro Val Gly Glu Ala Asp Pro Tyr Arg Val Lys
            500                 505                 510

Met Lys Leu Cys Ile Leu Leu His Ala Phe Ser Thr Arg Val Val Thr
        515                 520                 525

Ile Asn Arg Val Met Gly Tyr Leu Ser Ser Ala Gly Ser Gly Val Lys
        530                 535                 540

Leu Glu Ser Met Gly Ile Tyr Gln Ile Leu Ala Ile Tyr Ser Thr Val
545                 550                 555                 560

Ala Ser Ser Leu Val Leu Leu Val Ser Leu Gly Ala Ile Ser Phe Trp
                565                 570                 575

Met Cys Ser Asn Gly Ser Leu Gln Cys Arg Ile Cys Ile
                580                 585
```

<210> SEQ ID NO 9
<211> LENGTH: 859
<212> TYPE: PRT
<213> ORGANISM: Artificial Sequence
<220> FEATURE:
<223> OTHER INFORMATION: Synthetic sequence, fused polypeptide
      comprising mouse IL-12 (p40-p35), human IgG4CH3 and human TLR4(TM-
      TIR)

<400> SEQUENCE: 9

```
Met Ala Cys Pro Gln Lys Leu Thr Ile Ser Trp Phe Ala Ile Val Leu
1               5                   10                  15

Leu Val Ser Pro Leu Met Ala Met Trp Glu Leu Glu Lys Asp Val Tyr
            20                  25                  30

Val Val Glu Val Asp Trp Thr Pro Asp Ala Pro Gly Glu Thr Val Asn
        35                  40                  45

Leu Thr Cys Asp Thr Pro Glu Glu Asp Ile Thr Trp Thr Ser Asp
        50                  55                  60

Gln Arg His Gly Val Ile Gly Ser Gly Lys Thr Leu Thr Ile Thr Val
65                  70                  75                  80

Lys Glu Phe Leu Asp Ala Gly Gln Tyr Thr Cys His Lys Gly Gly Glu
                85                  90                  95

Thr Leu Ser His Ser His Leu Leu Leu His Lys Lys Glu Asn Gly Ile
            100                 105                 110

Trp Ser Thr Glu Ile Leu Lys Asn Phe Lys Asn Lys Thr Phe Leu Lys
        115                 120                 125

Cys Glu Ala Pro Asn Tyr Ser Gly Arg Phe Thr Cys Ser Trp Leu Val
    130                 135                 140

Gln Arg Asn Met Asp Leu Lys Phe Asn Ile Lys Ser Ser Ser Ser Pro
145                 150                 155                 160
```

-continued

Pro Asp Ser Arg Ala Val Thr Cys Gly Met Ala Ser Leu Ser Ala Glu
            165                 170                 175

Lys Val Thr Leu Asp Gln Arg Asp Tyr Glu Lys Tyr Ser Val Ser Cys
            180                 185                 190

Gln Glu Asp Val Thr Cys Pro Thr Ala Glu Glu Thr Leu Pro Ile Glu
            195                 200                 205

Leu Ala Leu Glu Ala Arg Gln Gln Asn Lys Tyr Glu Asn Tyr Ser Thr
            210                 215                 220

Ser Phe Phe Ile Arg Asp Ile Ile Lys Pro Asp Pro Pro Lys Asn Leu
225                 230                 235                 240

Gln Met Lys Pro Leu Lys Asn Ser Gln Val Glu Val Ser Trp Glu Tyr
            245                 250                 255

Pro Asp Ser Trp Ser Thr Pro His Ser Tyr Phe Ser Leu Lys Phe Phe
            260                 265                 270

Val Arg Ile Gln Arg Lys Lys Glu Lys Met Lys Glu Thr Glu Glu Gly
            275                 280                 285

Cys Asn Gln Lys Gly Ala Phe Leu Val Glu Lys Thr Ser Thr Glu Val
            290                 295                 300

Gln Cys Lys Gly Gly Asn Val Cys Val Gln Ala Gln Asp Arg Tyr Tyr
305                 310                 315                 320

Asn Ser Ser Cys Ser Lys Trp Ala Cys Val Pro Cys Arg Val Arg Ser
            325                 330                 335

Val Pro Gly Val Gly Val Pro Gly Val Gly Arg Val Ile Pro Val Ser
            340                 345                 350

Gly Pro Ala Arg Cys Leu Ser Gln Ser Arg Asn Leu Leu Lys Thr Thr
            355                 360                 365

Asp Asp Met Val Lys Thr Ala Arg Glu Lys Leu Lys His Tyr Ser Cys
            370                 375                 380

Thr Ala Glu Asp Ile Asp His Glu Asp Ile Thr Arg Asp Gln Thr Ser
385                 390                 395                 400

Thr Leu Lys Thr Cys Leu Pro Leu Glu Leu His Lys Asn Glu Ser Cys
            405                 410                 415

Leu Ala Thr Arg Glu Thr Ser Ser Thr Thr Arg Gly Ser Cys Leu Pro
            420                 425                 430

Pro Gln Lys Thr Ser Leu Met Met Thr Leu Cys Leu Gly Ser Ile Tyr
            435                 440                 445

Glu Asp Leu Lys Met Tyr Gln Thr Glu Phe Gln Ala Ile Asn Ala Ala
            450                 455                 460

Leu Gln Asn His Asn His Gln Gln Ile Ile Leu Asp Lys Gly Met Leu
465                 470                 475                 480

Val Ala Ile Asp Glu Leu Met Gln Ser Leu Asn His Asn Gly Glu Thr
            485                 490                 495

Leu Arg Gln Lys Pro Pro Val Gly Glu Ala Asp Pro Tyr Arg Val Lys
            500                 505                 510

Met Lys Leu Cys Ile Leu Leu His Ala Phe Ser Thr Arg Val Val Thr
            515                 520                 525

Ile Asn Arg Val Met Gly Tyr Leu Ser Ser Ala Gly Ser Gly Gln Pro
530                 535                 540

Arg Glu Pro Gln Val Tyr Thr Leu Pro Pro Ser Gln Glu Glu Met Thr
545                 550                 555                 560

Lys Asn Gln Val Ser Leu Thr Cys Leu Val Lys Gly Phe Tyr Pro Ser
            565                 570                 575

Asp Ile Ala Val Glu Trp Glu Ser Asn Gly Gln Pro Glu Asn Asn Tyr

```
                    580             585             590
Lys Thr Thr Pro Val Leu Asp Ser Asp Gly Ser Phe Phe Leu Tyr
            595             600             605

Ser Arg Leu Thr Val Asp Lys Ser Arg Trp Gln Gly Asn Val Phe
610             615             620

Ser Cys Ser Val Met His Glu Ala Leu His Asn His Tyr Thr Gln Lys
625             630             635             640

Ser Leu Ser Leu Ser Leu Gly Lys Gly Ser Lys Thr Ile Ile Gly Val
            645             650             655

Ser Val Leu Ser Val Leu Val Val Ser Val Val Ala Val Leu Val Tyr
            660             665             670

Lys Phe Tyr Phe His Leu Met Leu Leu Ala Gly Cys Ile Lys Tyr Gly
            675             680             685

Arg Gly Glu Asn Ile Tyr Asp Ala Phe Val Ile Tyr Ser Ser Gln Asp
            690             695             700

Glu Asp Trp Val Arg Asn Glu Leu Val Lys Asn Leu Glu Glu Gly Val
705             710             715             720

Pro Pro Phe Gln Leu Cys Leu His Tyr Arg Asp Phe Ile Pro Gly Val
            725             730             735

Ala Ile Ala Ala Asn Ile Ile His Glu Gly Phe His Lys Ser Arg Lys
            740             745             750

Val Ile Val Val Ser Gln His Phe Ile Gln Ser Arg Trp Cys Ile
            755             760             765

Phe Glu Tyr Glu Ile Ala Gln Thr Trp Gln Phe Leu Ser Ser Arg Ala
            770             775             780

Gly Ile Ile Phe Ile Val Leu Gln Lys Val Glu Lys Thr Leu Leu Arg
785             790             795             800

Gln Gln Val Glu Leu Tyr Arg Leu Leu Ser Arg Asn Thr Tyr Leu Glu
            805             810             815

Trp Glu Asp Ser Val Leu Gly Arg His Ile Phe Trp Arg Arg Leu Arg
            820             825             830

Lys Ala Leu Leu Asp Gly Lys Ser Trp Asn Pro Glu Gly Thr Val Gly
            835             840             845

Thr Gly Cys Asn Trp Gln Glu Ala Thr Ser Ile
    850             855
```

<210> SEQ ID NO 10
<211> LENGTH: 209
<212> TYPE: PRT
<213> ORGANISM: Artificial Sequence
<220> FEATURE:
<223> OTHER INFORMATION: Synthetic sequence, human TLR4(TM-TIR)

<400> SEQUENCE: 10

```
Lys Thr Ile Ile Gly Val Ser Val Leu Ser Val Leu Val Val Ser Val
1               5                   10                  15

Val Ala Val Leu Val Tyr Lys Phe Tyr Phe His Leu Met Leu Leu Ala
            20              25                  30

Gly Cys Ile Lys Tyr Gly Arg Gly Glu Asn Ile Tyr Asp Ala Phe Val
        35                  40                  45

Ile Tyr Ser Ser Gln Asp Glu Asp Trp Val Arg Asn Glu Leu Val Lys
    50                  55                  60

Asn Leu Glu Glu Gly Val Pro Pro Phe Gln Leu Cys Leu His Tyr Arg
65                  70                  75                  80

Asp Phe Ile Pro Gly Val Ala Ile Ala Ala Asn Ile Ile His Glu Gly
```

```
                    85                  90                  95
Phe His Lys Ser Arg Lys Val Ile Val Val Ser Gln His Phe Ile
            100                 105                 110
Gln Ser Arg Trp Cys Ile Phe Glu Tyr Glu Ile Ala Gln Thr Trp Gln
            115                 120                 125
Phe Leu Ser Ser Arg Ala Gly Ile Ile Phe Ile Leu Gln Lys Val
            130                 135                 140
Glu Lys Thr Leu Leu Arg Gln Gln Val Glu Leu Tyr Arg Leu Leu Ser
145                 150                 155                 160
Arg Asn Thr Tyr Leu Glu Trp Glu Asp Ser Val Leu Gly Arg His Ile
                165                 170                 175
Phe Trp Arg Arg Leu Arg Lys Ala Leu Leu Asp Gly Lys Ser Trp Asn
            180                 185                 190
Pro Glu Gly Thr Val Gly Thr Gly Cys Asn Trp Gln Glu Ala Thr Ser
            195                 200                 205
Ile

<210> SEQ ID NO 11
<211> LENGTH: 750
<212> TYPE: PRT
<213> ORGANISM: Artificial Sequence
<220> FEATURE:
<223> OTHER INFORMATION: Synthetic sequence, fused polypeptide
      comprising mouse IL-12(p40-p35) and human TLR4(TM-TIR)

<400> SEQUENCE: 11

Met Ala Cys Pro Gln Lys Leu Thr Ile Ser Trp Phe Ala Ile Val Leu
1               5                   10                  15
Leu Val Ser Pro Leu Met Ala Met Trp Glu Leu Glu Lys Asp Val Tyr
            20                  25                  30
Val Val Glu Val Asp Trp Thr Pro Asp Ala Pro Gly Glu Thr Val Asn
            35                  40                  45
Leu Thr Cys Asp Thr Pro Glu Glu Asp Ile Thr Trp Thr Ser Asp
        50                  55                  60
Gln Arg His Gly Val Ile Gly Ser Gly Lys Thr Leu Thr Ile Thr Val
65                  70                  75                  80
Lys Glu Phe Leu Asp Ala Gly Gln Tyr Thr Cys His Lys Gly Gly Glu
                85                  90                  95
Thr Leu Ser His Ser His Leu Leu Leu His Lys Lys Glu Asn Gly Ile
            100                 105                 110
Trp Ser Thr Glu Ile Leu Lys Asn Phe Lys Asn Lys Thr Phe Leu Lys
            115                 120                 125
Cys Glu Ala Pro Asn Tyr Ser Gly Arg Phe Thr Cys Ser Trp Leu Val
            130                 135                 140
Gln Arg Asn Met Asp Leu Lys Phe Asn Ile Lys Ser Ser Ser Pro
145                 150                 155                 160
Pro Asp Ser Arg Ala Val Thr Cys Gly Met Ala Ser Leu Ser Ala Glu
                165                 170                 175
Lys Val Thr Leu Asp Gln Arg Asp Tyr Glu Lys Tyr Ser Val Ser Cys
            180                 185                 190
Gln Glu Asp Val Thr Cys Pro Thr Ala Glu Glu Thr Leu Pro Ile Glu
            195                 200                 205
Leu Ala Leu Glu Ala Arg Gln Gln Asn Lys Tyr Glu Asn Tyr Ser Thr
            210                 215                 220
Ser Phe Phe Ile Arg Asp Ile Ile Lys Pro Asp Pro Pro Lys Asn Leu
```

-continued

```
225                 230                 235                 240
Gln Met Lys Pro Leu Lys Asn Ser Gln Val Glu Val Ser Trp Glu Tyr
                245                 250                 255
Pro Asp Ser Trp Ser Thr Pro His Ser Tyr Phe Ser Leu Lys Phe Phe
                260                 265                 270
Val Arg Ile Gln Arg Lys Lys Glu Lys Met Lys Glu Thr Glu Glu Gly
                275                 280                 285
Cys Asn Gln Lys Gly Ala Phe Leu Val Glu Lys Thr Ser Thr Glu Val
                290                 295                 300
Gln Cys Lys Gly Gly Asn Val Cys Val Gln Ala Gln Asp Arg Tyr Tyr
305                 310                 315                 320
Asn Ser Ser Cys Ser Lys Trp Ala Cys Val Pro Cys Arg Val Arg Ser
                325                 330                 335
Val Pro Gly Val Gly Val Pro Gly Val Gly Arg Val Ile Pro Val Ser
                340                 345                 350
Gly Pro Ala Arg Cys Leu Ser Gln Ser Arg Asn Leu Leu Lys Thr Thr
                355                 360                 365
Asp Asp Met Val Lys Thr Ala Arg Glu Lys Leu Lys His Tyr Ser Cys
370                 375                 380
Thr Ala Glu Asp Ile Asp His Glu Asp Ile Thr Arg Asp Gln Thr Ser
385                 390                 395                 400
Thr Leu Lys Thr Cys Leu Pro Leu Glu Leu His Lys Asn Glu Ser Cys
                405                 410                 415
Leu Ala Thr Arg Glu Thr Ser Ser Thr Thr Arg Gly Ser Cys Leu Pro
                420                 425                 430
Pro Gln Lys Thr Ser Leu Met Met Thr Leu Cys Leu Gly Ser Ile Tyr
                435                 440                 445
Glu Asp Leu Lys Met Tyr Gln Thr Glu Phe Gln Ala Ile Asn Ala Ala
                450                 455                 460
Leu Gln Asn His Asn His Gln Gln Ile Ile Leu Asp Lys Gly Met Leu
465                 470                 475                 480
Val Ala Ile Asp Glu Leu Met Gln Ser Leu Asn His Asn Gly Glu Thr
                485                 490                 495
Leu Arg Gln Lys Pro Pro Val Gly Glu Ala Asp Pro Tyr Arg Val Lys
                500                 505                 510
Met Lys Leu Cys Ile Leu Leu His Ala Phe Ser Thr Arg Val Val Thr
                515                 520                 525
Ile Asn Arg Val Met Gly Tyr Leu Ser Ser Ala Gly Ser Lys Thr Ile
                530                 535                 540
Ile Gly Val Ser Val Leu Ser Val Leu Val Ser Val Val Ala Val
545                 550                 555                 560
Leu Val Tyr Lys Phe Tyr Phe His Leu Met Leu Leu Ala Gly Cys Ile
                565                 570                 575
Lys Tyr Gly Arg Gly Glu Asn Ile Tyr Asp Ala Phe Val Ile Tyr Ser
                580                 585                 590
Ser Gln Asp Glu Asp Trp Val Arg Asn Glu Leu Val Lys Asn Leu Glu
                595                 600                 605
Glu Gly Val Pro Pro Phe Gln Leu Cys Leu His Tyr Arg Asp Phe Ile
                610                 615                 620
Pro Gly Val Ala Ile Ala Ala Asn Ile Ile His Glu Gly Phe His Lys
625                 630                 635                 640
Ser Arg Lys Val Ile Val Val Ser Gln His Phe Ile Gln Ser Arg
                645                 650                 655
```

```
Trp Cys Ile Phe Glu Tyr Glu Ile Ala Gln Thr Trp Gln Phe Leu Ser
            660                 665                 670

Ser Arg Ala Gly Ile Ile Phe Ile Val Leu Gln Lys Val Glu Lys Thr
            675                 680                 685

Leu Leu Arg Gln Gln Val Glu Leu Tyr Arg Leu Leu Ser Arg Asn Thr
            690                 695                 700

Tyr Leu Glu Trp Glu Asp Ser Val Leu Gly Arg His Ile Phe Trp Arg
705                 710                 715                 720

Arg Leu Arg Lys Ala Leu Leu Asp Gly Lys Ser Trp Asn Pro Glu Gly
                725                 730                 735

Thr Val Gly Thr Gly Cys Asn Trp Gln Glu Ala Thr Ser Ile
                740                 745                 750

<210> SEQ ID NO 12
<211> LENGTH: 698
<212> TYPE: PRT
<213> ORGANISM: Artificial Sequence
<220> FEATURE:
<223> OTHER INFORMATION: Synthetic sequence, fused polypeptide
      comprising mouse IL-12(p40-p35), mouse IgG4CH3 and influenza
      HA(Flex-TM-Cyt)

<400> SEQUENCE: 12

Met Ala Cys Pro Gln Lys Leu Thr Ile Ser Trp Phe Ala Ile Val Leu
1               5                   10                  15

Leu Val Ser Pro Leu Met Ala Met Trp Glu Leu Glu Lys Asp Val Tyr
                20                  25                  30

Val Val Glu Val Asp Trp Thr Pro Asp Ala Pro Gly Glu Thr Val Asn
            35                  40                  45

Leu Thr Cys Asp Thr Pro Glu Glu Asp Ile Thr Trp Thr Ser Asp
        50                  55                  60

Gln Arg His Gly Val Ile Gly Ser Gly Lys Thr Leu Thr Ile Thr Val
65              70                  75                  80

Lys Glu Phe Leu Asp Ala Gly Gln Tyr Thr Cys His Lys Gly Gly Glu
                85                  90                  95

Thr Leu Ser His Ser His Leu Leu Leu His Lys Lys Glu Asn Gly Ile
            100                 105                 110

Trp Ser Thr Glu Ile Leu Lys Asn Phe Lys Asn Lys Thr Phe Leu Lys
            115                 120                 125

Cys Glu Ala Pro Asn Tyr Ser Gly Arg Phe Thr Cys Ser Trp Leu Val
        130                 135                 140

Gln Arg Asn Met Asp Leu Lys Phe Asn Ile Lys Ser Ser Ser Ser Pro
145                 150                 155                 160

Pro Asp Ser Arg Ala Val Thr Cys Gly Met Ala Ser Leu Ser Ala Glu
                165                 170                 175

Lys Val Thr Leu Asp Gln Arg Asp Tyr Glu Lys Tyr Ser Val Ser Cys
            180                 185                 190

Gln Glu Asp Val Thr Cys Pro Thr Ala Glu Glu Thr Leu Pro Ile Glu
        195                 200                 205

Leu Ala Leu Glu Ala Arg Gln Gln Asn Lys Tyr Glu Asn Tyr Ser Thr
    210                 215                 220

Ser Phe Phe Ile Arg Asp Ile Ile Lys Pro Asp Pro Pro Lys Asn Leu
225                 230                 235                 240

Gln Met Lys Pro Leu Lys Asn Ser Gln Val Glu Val Ser Trp Glu Tyr
                245                 250                 255
```

```
Pro Asp Ser Trp Ser Thr Pro His Ser Tyr Phe Ser Leu Lys Phe Phe
            260                 265                 270

Val Arg Ile Gln Arg Lys Lys Glu Lys Met Lys Glu Thr Glu Glu Gly
            275                 280                 285

Cys Asn Gln Lys Gly Ala Phe Leu Val Glu Lys Thr Ser Thr Glu Val
            290                 295                 300

Gln Cys Lys Gly Gly Asn Val Cys Val Gln Ala Gln Asp Arg Tyr Tyr
305                 310                 315                 320

Asn Ser Ser Cys Ser Lys Trp Ala Cys Val Pro Cys Arg Val Arg Ser
                325                 330                 335

Val Pro Gly Val Gly Val Pro Gly Val Gly Arg Val Ile Pro Val Ser
            340                 345                 350

Gly Pro Ala Arg Cys Leu Ser Gln Ser Arg Asn Leu Leu Lys Thr Thr
            355                 360                 365

Asp Asp Met Val Lys Thr Ala Arg Glu Lys Leu Lys His Tyr Ser Cys
            370                 375                 380

Thr Ala Glu Asp Ile Asp His Glu Asp Ile Thr Arg Asp Gln Thr Ser
385                 390                 395                 400

Thr Leu Lys Thr Cys Leu Pro Leu Glu Leu His Lys Asn Glu Ser Cys
                405                 410                 415

Leu Ala Thr Arg Glu Thr Ser Ser Thr Thr Arg Gly Ser Cys Leu Pro
            420                 425                 430

Pro Gln Lys Thr Ser Leu Met Met Thr Leu Cys Leu Gly Ser Ile Tyr
            435                 440                 445

Glu Asp Leu Lys Met Tyr Gln Thr Glu Phe Gln Ala Ile Asn Ala Ala
450                 455                 460

Leu Gln Asn His Asn His Gln Gln Ile Ile Leu Asp Lys Gly Met Leu
465                 470                 475                 480

Val Ala Ile Asp Glu Leu Met Gln Ser Leu Asn His Asn Gly Glu Thr
                485                 490                 495

Leu Arg Gln Lys Pro Pro Val Gly Glu Ala Asp Pro Tyr Arg Val Lys
            500                 505                 510

Met Lys Leu Cys Ile Leu Leu His Ala Phe Ser Thr Arg Val Val Thr
            515                 520                 525

Ile Asn Arg Val Met Gly Tyr Leu Ser Ser Ala Gly Ser Gly Arg Pro
530                 535                 540

Lys Ala Pro Gln Val Tyr Thr Ile Pro Pro Lys Glu Gln Met Ala
545                 550                 555                 560

Lys Asp Lys Val Ser Leu Thr Cys Met Ile Thr Asn Phe Phe Pro Glu
                565                 570                 575

Asp Ile Thr Val Glu Trp Gln Trp Asn Gly Gln Pro Ala Glu Asn Tyr
            580                 585                 590

Lys Asn Thr Gln Pro Ile Met Asp Thr Asp Gly Ser Tyr Phe Val Tyr
            595                 600                 605

Ser Lys Leu Asn Val Gln Lys Ser Asn Trp Glu Ala Gly Asn Thr Phe
            610                 615                 620

Thr Cys Ser Val Leu His Glu Gly Leu His Asn His Thr Glu Lys
625                 630                 635                 640

Ser Leu Ser His Ser Pro Gly Lys Gly Ser Val Lys Leu Glu Ser
                645                 650                 655

Met Gly Ile Tyr Gln Ile Leu Ala Ile Tyr Ser Thr Val Ala Ser Ser
            660                 665                 670

Leu Val Leu Leu Val Ser Leu Gly Ala Ile Ser Phe Trp Met Cys Ser
```

-continued

```
                675                 680                 685

Asn Gly Ser Leu Gln Cys Arg Ile Cys Ile
    690                 695

<210> SEQ ID NO 13
<211> LENGTH: 106
<212> TYPE: PRT
<213> ORGANISM: Artificial Sequence
<220> FEATURE:
<223> OTHER INFORMATION: Synthetic sequence, mouse IgG4CH3

<400> SEQUENCE: 13

Gly Arg Pro Lys Ala Pro Gln Val Tyr Thr Ile Pro Pro Pro Lys Glu
1               5                   10                  15

Gln Met Ala Lys Asp Lys Val Ser Leu Thr Cys Met Ile Thr Asn Phe
            20                  25                  30

Phe Pro Glu Asp Ile Thr Val Glu Trp Gln Trp Asn Gly Gln Pro Ala
        35                  40                  45

Glu Asn Tyr Lys Asn Thr Gln Pro Ile Met Asp Thr Asp Gly Ser Tyr
    50                  55                  60

Phe Val Tyr Ser Lys Leu Asn Val Gln Lys Ser Asn Trp Glu Ala Gly
65                  70                  75                  80

Asn Thr Phe Thr Cys Ser Val Leu His Glu Gly Leu His Asn His His
                85                  90                  95

Thr Glu Lys Ser Leu Ser His Ser Pro Gly
            100                 105

<210> SEQ ID NO 14
<211> LENGTH: 535
<212> TYPE: PRT
<213> ORGANISM: Artificial Sequence
<220> FEATURE:
<223> OTHER INFORMATION: Synthetic sequence, fused polypeptide
      comprising human IL-12B p40, linker and human IL-12A p35 without
      singal sequence (Human IL-12(p40-p35))

<400> SEQUENCE: 14

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
```

```
                165                 170                 175
Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Val Pro Gly Val Gly Val Pro Gly
                325                 330                 335

Val Gly Arg Asn Leu Pro Val Ala Thr Pro Asp Pro Gly Met Phe Pro
            340                 345                 350

Cys Leu His His Ser Gln Asn Leu Leu Arg Ala Val Ser Asn Met Leu
        355                 360                 365

Gln Lys Ala Arg Gln Thr Leu Glu Phe Tyr Pro Cys Thr Ser Glu Glu
        370                 375                 380

Ile Asp His Glu Asp Ile Thr Lys Asp Lys Thr Ser Thr Val Glu Ala
385                 390                 395                 400

Cys Leu Pro Leu Glu Leu Thr Lys Asn Glu Ser Cys Leu Asn Ser Arg
                405                 410                 415

Glu Thr Ser Phe Ile Thr Asn Gly Ser Cys Leu Ala Ser Arg Lys Thr
            420                 425                 430

Ser Phe Met Met Ala Leu Cys Leu Ser Ser Ile Tyr Glu Asp Leu Lys
        435                 440                 445

Met Tyr Gln Val Glu Phe Lys Thr Met Asn Ala Lys Leu Leu Met Asp
        450                 455                 460

Pro Lys Arg Gln Ile Phe Leu Asp Gln Asn Met Leu Ala Val Ile Asp
465                 470                 475                 480

Glu Leu Met Gln Ala Leu Asn Phe Asn Ser Glu Thr Val Pro Gln Lys
                485                 490                 495

Ser Ser Leu Glu Glu Pro Asp Phe Tyr Lys Thr Lys Ile Lys Leu Cys
            500                 505                 510

Ile Leu Leu His Ala Phe Arg Ile Arg Ala Val Thr Ile Asp Arg Val
        515                 520                 525

Met Ser Tyr Leu Asn Ala Ser
530                 535

<210> SEQ ID NO 15
<211> LENGTH: 328
<212> TYPE: PRT
<213> ORGANISM: Artificial Sequence
<220> FEATURE:
<223> OTHER INFORMATION: Synthetic sequence, human IL-12B(p40)
```

```
<400> SEQUENCE: 15

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 16
<211> LENGTH: 22
<212> TYPE: PRT
<213> ORGANISM: Artificial Sequence
<220> FEATURE:
<223> OTHER INFORMATION: Synthetic sequence, signal sequence of human
      IL-12A (p35)

<400> SEQUENCE: 16

Met Cys Pro Ala Arg Ser Leu Leu Leu Val Ala Thr Leu Val Leu Leu
1               5                   10                  15
```

```
Asp His Leu Ser Leu Ala
            20

<210> SEQ ID NO 17
<211> LENGTH: 197
<212> TYPE: PRT
<213> ORGANISM: Artificial Sequence
<220> FEATURE:
<223> OTHER INFORMATION: Synthetic sequence, human IL-12A (p35) without
      signal sequence

<400> SEQUENCE: 17

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
            195

<210> SEQ ID NO 18
<211> LENGTH: 694
<212> TYPE: PRT
<213> ORGANISM: Artificial Sequence
<220> FEATURE:
<223> OTHER INFORMATION: Synthetic sequence, fused polypeptide
      comprising human IL-12(p40-p35), human IgG4CH3 and Influenza
      HA(Flex-TM-Cyt)

<400> SEQUENCE: 18

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80
```

-continued

```
Glu Phe Gly Asp Ala Gly Gln Tyr Thr Cys His Lys Gly Gly Glu Val
                 85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
            130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Cys Pro Ala Ala Glu Glu Ser Leu Pro Ile
                195                 200                 205

Glu Val Met Val Asp Ala Val His Lys Leu Lys Tyr Glu Asn Tyr Thr
            210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
            290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Val Pro Gly Val Gly Val Pro Gly
                325                 330                 335

Val Gly Arg Asn Leu Pro Val Ala Thr Pro Asp Pro Gly Met Phe Pro
            340                 345                 350

Cys Leu His His Ser Gln Asn Leu Leu Arg Ala Val Ser Asn Met Leu
            355                 360                 365

Gln Lys Ala Arg Gln Thr Leu Glu Phe Tyr Pro Cys Thr Ser Glu Glu
            370                 375                 380

Ile Asp His Glu Asp Ile Thr Lys Asp Lys Thr Ser Thr Val Glu Ala
385                 390                 395                 400

Cys Leu Pro Leu Glu Leu Thr Lys Asn Glu Ser Cys Leu Asn Ser Arg
                405                 410                 415

Glu Thr Ser Phe Ile Thr Asn Gly Ser Cys Leu Ala Ser Arg Lys Thr
                420                 425                 430

Ser Phe Met Met Ala Leu Cys Leu Ser Ser Ile Tyr Glu Asp Leu Lys
            435                 440                 445

Met Tyr Gln Val Glu Phe Lys Thr Met Asn Ala Lys Leu Leu Met Asp
        450                 455                 460

Pro Lys Arg Gln Ile Phe Leu Asp Gln Asn Met Leu Ala Val Ile Asp
465                 470                 475                 480

Glu Leu Met Gln Ala Leu Asn Phe Asn Ser Glu Thr Val Pro Gln Lys
                485                 490                 495
```

```
Ser Ser Leu Glu Glu Pro Asp Phe Tyr Lys Thr Lys Ile Lys Leu Cys
            500                 505                 510

Ile Leu Leu His Ala Phe Arg Ile Arg Ala Val Thr Ile Asp Arg Val
        515                 520                 525

Met Ser Tyr Leu Asn Ala Ser Gly Ser Gly Gln Pro Arg Glu Pro Gln
    530                 535                 540

Val Tyr Thr Leu Pro Pro Ser Gln Glu Glu Met Thr Lys Asn Gln Val
545                 550                 555                 560

Ser Leu Thr Cys Leu Val Lys Gly Phe Tyr Pro Ser Asp Ile Ala Val
                565                 570                 575

Glu Trp Glu Ser Asn Gly Gln Pro Glu Asn Asn Tyr Lys Thr Thr Pro
            580                 585                 590

Pro Val Leu Asp Ser Asp Gly Ser Phe Phe Leu Tyr Ser Arg Leu Thr
        595                 600                 605

Val Asp Lys Ser Arg Trp Gln Glu Gly Asn Val Phe Ser Cys Ser Val
    610                 615                 620

Met His Glu Ala Leu His Asn His Tyr Thr Gln Lys Ser Leu Ser Leu
625                 630                 635                 640

Ser Leu Gly Lys Gly Ser Gly Val Lys Leu Glu Ser Met Gly Ile Tyr
                645                 650                 655

Gln Ile Leu Ala Ile Tyr Ser Thr Val Ala Ser Ser Leu Val Leu Leu
            660                 665                 670

Val Ser Leu Gly Ala Ile Ser Phe Trp Met Cys Ser Asn Gly Ser Leu
        675                 680                 685

Gln Cys Arg Ile Cys Ile
    690

<210> SEQ ID NO 19
<211> LENGTH: 35
<212> TYPE: DNA
<213> ORGANISM: Artificial Sequence
<220> FEATURE:
<223> OTHER INFORMATION: Synthetic sequence, SG promoter

<400> SEQUENCE: 19
cctgaatgga ctacgacata gtctagtccg ccaag                          35

<210> SEQ ID NO 20
<211> LENGTH: 44
<212> TYPE: DNA
<213> ORGANISM: Artificial Sequence
<220> FEATURE:
<223> OTHER INFORMATION: Synthetic sequence, 5'UTR

<400> SEQUENCE: 20
ataggcggcg catgagagaa gcccagacca attacctacc caaa                44

<210> SEQ ID NO 21
<211> LENGTH: 125
<212> TYPE: DNA
<213> ORGANISM: Artificial Sequence
<220> FEATURE:
<223> OTHER INFORMATION: Synthetic sequence, 3'UTR

<400> SEQUENCE: 21
gcgatcgcat acagcagcaa ttggcaagct gcttacatag aactcgcggc gattggcatg  60
ccgccttaaa attttatttt tatttttctt ttcttttccg aatcggattt tgttttaat  120 atttc                                                             125
```

<210> SEQ ID NO 22
<211> LENGTH: 55
<212> TYPE: DNA
<213> ORGANISM: Artificial Sequence
<220> FEATURE:
<223> OTHER INFORMATION: Synthetic sequence, poly A tail

<400> SEQUENCE: 22
aaaaaaaaaa aaaaaaaaaa aaaaaaaaaa aaaaaaaaaa aaaaaaaaaa aaaaa         55

<210> SEQ ID NO 23
<211> LENGTH: 2493
<212> TYPE: PRT
<213> ORGANISM: Artificial Sequence
<220> FEATURE:
<223> OTHER INFORMATION: Synthetic sequence, VEEV TC-83 Replicon nsP1-4
<220> FEATURE:
<221> NAME/KEY: misc_feature
<222> LOCATION: (1880)..(1880)
<223> OTHER INFORMATION: Xaa can be any naturally occurring amino acid

<400> SEQUENCE: 23

Met Glu Lys Val His Val Asp Ile Glu Glu Asp Ser Pro Phe Leu Arg
1 5 10 15

Ala Leu Gln Arg Ser Phe Pro Gln Phe Glu Val Glu Ala Lys Gln Val
20 25 30

Thr Asp Asn Asp His Ala Asn Ala Arg Ala Phe Ser His Leu Ala Ser
35 40 45

Lys Leu Ile Glu Thr Glu Val Asp Pro Ser Asp Thr Ile Leu Asp Ile
50 55 60

Gly Ser Ala Pro Ala Arg Arg Met Tyr Ser Lys His Lys Tyr His Cys
65 70 75 80

Ile Cys Pro Met Arg Cys Ala Glu Asp Pro Asp Arg Leu Tyr Lys Tyr
85 90 95

Ala Thr Lys Leu Lys Lys Asn Cys Lys Glu Ile Thr Asp Lys Glu Leu
100 105 110

Asp Lys Lys Met Lys Glu Leu Ala Ala Val Met Ser Asp Pro Asp Leu
115 120 125

Glu Thr Glu Thr Met Cys Leu His Asp Asp Glu Ser Cys Arg Tyr Glu
130 135 140

Gly Gln Val Ala Val Tyr Gln Asp Val Tyr Ala Val Asp Gly Pro Thr
145 150 155 160

Ser Leu Tyr His Gln Ala Asn Lys Gly Val Arg Val Ala Tyr Trp Ile
165 170 175

Gly Phe Asp Thr Thr Pro Phe Met Phe Lys Asn Leu Ala Gly Ala Tyr
180 185 190

Pro Ser Tyr Ser Thr Asn Trp Ala Asp Glu Thr Val Leu Thr Ala Arg
195 200 205

Asn Ile Gly Leu Cys Ser Ser Asp Val Met Glu Arg Ser Arg Arg Gly
210 215 220

Met Ser Ile Leu Arg Lys Lys Tyr Leu Lys Pro Ser Asn Asn Val Leu
225 230 235 240

Phe Ser Val Gly Ser Thr Ile Tyr His Glu Lys Arg Asp Leu Leu Arg
245 250 255

Ser Trp His Leu Pro Ser Val Phe His Leu Arg Gly Lys Gln Asn Tyr
260 265 270

Thr Cys Arg Cys Glu Thr Ile Val Ser Cys Asp Gly Tyr Val Val Lys
275 280 285

```
Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
450                 455                 460

Arg Thr Arg Ile Arg Lys Met Leu Glu Glu His Lys Glu Pro Ser Pro
465                 470                 475                 480

Leu Ile Thr Ala Glu Asp Ile Gln Glu Ala Lys Cys Ala Ala Asp Glu
                485                 490                 495

Ala Lys Glu Val Arg Glu Ala Glu Glu Leu Arg Ala Ala Leu Pro Pro
            500                 505                 510

Leu Ala Ala Asp Phe Glu Glu Pro Thr Leu Glu Ala Asp Val Asp Leu
        515                 520                 525

Met Leu Gln Glu Ala Gly Ala Gly Ser Val Glu Thr Pro Arg Gly Leu
530                 535                 540

Ile Lys Val Thr Ser Tyr Ala Gly Glu Asp Lys Ile Gly Ser Tyr Ala
545                 550                 555                 560

Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Pro Glu
        595                 600                 605

Gly His Ala Ile Pro Val Gln Asp Phe Gln Ala Leu Ser Glu Ser Ala
610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
690                 695                 700
```

-continued

```
Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
            725                 730                 735

Lys Lys Asp Leu Val Val Ser Ala Lys Lys Glu Asn Cys Ala Glu Ile
                740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
            805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Arg Met
    850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
            885                 890                 895

Trp Val Lys Gln Leu Gln Ile Asp Tyr Lys Gly Asn Glu Ile Met Thr
        900                 905                 910

Ala Ala Ala Ser Gln Gly Leu Thr Arg Lys Gly Val Tyr Ala Val Arg
    915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Ile Leu Thr Ala Lys Tyr Pro Gly Asn
            965                 970                 975

Phe Thr Ala Thr Ile Glu Glu Trp Gln Ala Glu His Asp Ala Ile Met
            980                 985                 990

Arg His Ile Leu Glu Arg Pro Asp Pro Thr Asp Val Phe Gln Asn Lys
        995                 1000                1005

Ala Asn Val Cys Trp Ala Lys Ala Leu Val Pro Val Leu Lys Thr
    1010                1015                1020

Ala Gly Ile Asp Met Thr Thr Glu Gln Trp Asn Thr Val Asp Tyr
    1025                1030                1035

Phe Glu Thr Asp Lys Ala His Ser Ala Glu Ile Val Leu Asn Gln
    1040                1045                1050

Leu Cys Val Arg Phe Phe Gly Leu Asp Leu Asp Ser Gly Leu Phe
    1055                1060                1065

Ser Ala Pro Thr Val Pro Leu Ser Ile Arg Asn Asn His Trp Asp
    1070                1075                1080

Asn Ser Pro Ser Pro Asn Met Tyr Gly Leu Asn Lys Glu Val Val
    1085                1090                1095

Arg Gln Leu Ser Arg Arg Tyr Pro Gln Leu Pro Arg Ala Val Ala
    1100                1105                1110

Thr Gly Arg Val Tyr Asp Met Asn Thr Gly Thr Leu Arg Asn Tyr
```

-continued

```
            1115                1120                1125

Asp Pro Arg Ile Asn Leu Val Pro Val Asn Arg Arg Leu Pro His
    1130                1135                1140

Ala Leu Val Leu His His Asn Glu His Pro Gln Ser Asp Phe Ser
    1145                1150                1155

Ser Phe Val Ser Lys Leu Lys Gly Arg Thr Val Leu Val Val Gly
    1160                1165                1170

Glu Lys Leu Ser Val Pro Gly Lys Lys Val Asp Trp Leu Ser Asp
    1175                1180                1185

Gln Pro Glu Ala Thr Phe Arg Ala Arg Leu Asp Leu Gly Ile Pro
    1190                1195                1200

Gly Asp Val Pro Lys Tyr Asp Ile Val Phe Ile Asn Val Arg Thr
    1205                1210                1215

Pro Tyr Lys Tyr His His Tyr Gln Gln Cys Glu Asp His Ala Ile
    1220                1225                1230

Lys Leu Ser Met Leu Thr Lys Lys Ala Cys Leu His Leu Asn Pro
    1235                1240                1245

Gly Gly Thr Cys Val Ser Ile Gly Tyr Gly Tyr Ala Asp Arg Ala
    1250                1255                1260

Ser Glu Ser Ile Ile Gly Ala Ile Ala Arg Gln Phe Lys Phe Ser
    1265                1270                1275

Arg Val Cys Lys Pro Lys Ser Ser His Glu Glu Thr Glu Val Leu
    1280                1285                1290

Phe Val Phe Ile Gly Tyr Asp Arg Lys Ala Arg Thr His Asn Pro
    1295                1300                1305

Tyr Lys Leu Ser Ser Thr Leu Thr Asn Ile Tyr Thr Gly Ser Arg
    1310                1315                1320

Leu His Glu Ala Gly Cys Ala Pro Ser Tyr His Val Val Arg Gly
    1325                1330                1335

Asp Ile Ala Thr Ala Thr Glu Gly Val Ile Ile Asn Ala Ala Asn
    1340                1345                1350

Ser Lys Gly Gln Pro Gly Gly Gly Val Cys Gly Ala Leu Tyr Lys
    1355                1360                1365

Lys Phe Pro Glu Ser Phe Asp Leu Gln Pro Ile Glu Val Gly Lys
    1370                1375                1380

Ala Arg Leu Val Lys Gly Ala Ala Lys His Ile Ile His Ala Val
    1385                1390                1395

Gly Pro Asn Phe Asn Lys Val Ser Glu Val Glu Gly Asp Lys Gln
    1400                1405                1410

Leu Ala Glu Ala Tyr Glu Ser Ile Ala Lys Ile Val Asn Asp Asn
    1415                1420                1425

Asn Tyr Lys Ser Val Ala Ile Pro Leu Leu Ser Thr Gly Ile Phe
    1430                1435                1440

Ser Gly Asn Lys Asp Arg Leu Thr Gln Ser Leu Asn His Leu Leu
    1445                1450                1455

Thr Ala Leu Asp Thr Thr Asp Ala Asp Val Ala Ile Tyr Cys Arg
    1460                1465                1470

Asp Lys Lys Trp Glu Met Thr Leu Lys Glu Ala Val Ala Arg Arg
    1475                1480                1485

Glu Ala Val Glu Glu Ile Cys Ile Ser Asp Asp Ser Ser Val Thr
    1490                1495                1500

Glu Pro Asp Ala Glu Leu Val Arg Val His Pro Lys Ser Ser Leu
    1505                1510                1515
```

```
Ala Gly Arg Lys Gly Tyr Ser Thr Ser Asp Gly Lys Thr Phe Ser
    1520                1525                1530

Tyr Leu Glu Gly Thr Lys Phe His Gln Ala Ala Lys Asp Ile Ala
    1535                1540                1545

Glu Ile Asn Ala Met Trp Pro Val Ala Thr Glu Ala Asn Glu Gln
    1550                1555                1560

Val Cys Met Tyr Ile Leu Gly Glu Ser Met Ser Ser Ile Arg Ser
    1565                1570                1575

Lys Cys Pro Val Glu Glu Ser Glu Ala Ser Thr Pro Pro Ser Thr
    1580                1585                1590

Leu Pro Cys Leu Cys Ile His Ala Met Thr Pro Glu Arg Val Gln
    1595                1600                1605

Arg Leu Lys Ala Ser Arg Pro Glu Gln Ile Thr Val Cys Ser Ser
    1610                1615                1620

Phe Pro Leu Pro Lys Tyr Arg Ile Thr Gly Val Gln Lys Ile Gln
    1625                1630                1635

Cys Ser Gln Pro Ile Leu Phe Ser Pro Lys Val Pro Ala Tyr Ile
    1640                1645                1650

His Pro Arg Lys Tyr Leu Val Glu Thr Pro Pro Val Glu Glu Thr
    1655                1660                1665

Pro Glu Ser Pro Ala Glu Asn Gln Ser Thr Glu Gly Thr Pro Glu
    1670                1675                1680

Gln Pro Ala Leu Val Asn Val Asp Ala Thr Arg Thr Arg Met Pro
    1685                1690                1695

Glu Pro Ile Ile Ile Glu Glu Glu Glu Glu Asp Ser Ile Ser Leu
    1700                1705                1710

Leu Ser Asp Gly Pro Thr His Gln Val Leu Gln Val Glu Ala Asp
    1715                1720                1725

Ile His Gly Ser Pro Ser Val Ser Ser Ser Ser Trp Ser Ile Pro
    1730                1735                1740

His Ala Ser Asp Phe Asp Val Asp Ser Leu Ser Ile Leu Asp Thr
    1745                1750                1755

Leu Asp Gly Ala Ser Val Thr Ser Gly Ala Val Ser Ala Glu Thr
    1760                1765                1770

Asn Ser Tyr Phe Ala Arg Ser Met Glu Phe Arg Ala Arg Pro Val
    1775                1780                1785

Pro Ala Pro Arg Thr Val Phe Arg Asn Pro Pro His Pro Ala Pro
    1790                1795                1800

Arg Thr Arg Thr Pro Pro Leu Ala His Ser Arg Ala Ser Ser Arg
    1805                1810                1815

Thr Ser Leu Val Ser Thr Pro Pro Gly Val Asn Arg Val Ile Thr
    1820                1825                1830

Arg Glu Glu Leu Glu Ala Leu Thr Pro Ser Arg Ala Pro Ser Arg
    1835                1840                1845

Ser Ala Ser Arg Thr Ser Leu Val Ser Asn Pro Pro Gly Val Asn
    1850                1855                1860

Arg Val Ile Thr Arg Glu Glu Phe Glu Ala Phe Val Ala Gln Gln
    1865                1870                1875

Gln Xaa Arg Phe Asp Ala Gly Ala Tyr Ile Phe Ser Ser Asp Thr
    1880                1885                1890

Gly Gln Gly His Leu Gln Gln Lys Ser Val Arg Gln Thr Val Leu
    1895                1900                1905
```

Ser Glu Val Val Leu Glu Arg Thr Glu Leu Glu Ile Ser Tyr Ala
1910                1915                1920

Pro Arg Leu Asp Gln Glu Lys Glu Glu Leu Leu Arg Lys Lys Leu
1925                1930                1935

Gln Leu Asn Pro Thr Pro Ala Asn Arg Ser Arg Tyr Gln Ser Arg
1940                1945                1950

Arg Val Glu Asn Met Lys Ala Ile Thr Ala Arg Arg Ile Leu Gln
1955                1960                1965

Gly Leu Gly His Tyr Leu Lys Ala Glu Gly Lys Val Glu Cys Tyr
1970                1975                1980

Arg Thr Leu His Pro Val Pro Leu Tyr Ser Ser Ser Val Asn Arg
1985                1990                1995

Ala Phe Ser Ser Pro Lys Val Ala Val Glu Ala Cys Asn Ala Met
2000                2005                2010

Leu Lys Glu Asn Phe Pro Thr Val Ala Ser Tyr Cys Ile Ile Pro
2015                2020                2025

Glu Tyr Asp Ala Tyr Leu Asp Met Val Asp Gly Ala Ser Cys Cys
2030                2035                2040

Leu Asp Thr Ala Ser Phe Cys Pro Ala Lys Leu Arg Ser Phe Pro
2045                2050                2055

Lys Lys His Ser Tyr Leu Glu Pro Thr Ile Arg Ser Ala Val Pro
2060                2065                2070

Ser Ala Ile Gln Asn Thr Leu Gln Asn Val Leu Ala Ala Ala Thr
2075                2080                2085

Lys Arg Asn Cys Asn Val Thr Gln Met Arg Glu Leu Pro Val Leu
2090                2095                2100

Asp Ser Ala Ala Phe Asn Val Glu Cys Phe Lys Lys Tyr Ala Cys
2105                2110                2115

Asn Asn Glu Tyr Trp Glu Thr Phe Lys Glu Asn Pro Ile Arg Leu
2120                2125                2130

Thr Glu Glu Asn Val Val Asn Tyr Ile Thr Lys Leu Lys Gly Pro
2135                2140                2145

Lys Ala Ala Ala Leu Phe Ala Lys Thr His Asn Leu Asn Met Leu
2150                2155                2160

Gln Asp Ile Pro Met Asp Arg Phe Val Met Asp Leu Lys Arg Asp
2165                2170                2175

Val Lys Val Thr Pro Gly Thr Lys His Thr Glu Glu Arg Pro Lys
2180                2185                2190

Val Gln Val Ile Gln Ala Ala Asp Pro Leu Ala Thr Ala Asp Leu
2195                2200                2205

Cys Gly Ile His Arg Glu Leu Val Arg Arg Leu Asn Ala Val Leu
2210                2215                2220

Leu Pro Asn Ile His Thr Leu Phe Asp Met Ser Ala Glu Asp Phe
2225                2230                2235

Asp Ala Ile Ile Ala Glu His Phe Gln Pro Gly Asp Cys Val Leu
2240                2245                2250

Glu Thr Asp Ile Ala Ser Phe Asp Lys Ser Glu Asp Asp Ala Met
2255                2260                2265

Ala Leu Thr Ala Leu Met Ile Leu Glu Asp Leu Gly Val Asp Ala
2270                2275                2280

Glu Leu Leu Thr Leu Ile Glu Ala Ala Phe Gly Glu Ile Ser Ser
2285                2290                2295

Ile His Leu Pro Thr Lys Thr Lys Phe Lys Phe Gly Ala Met Met

-continued

```
                2300                2305                2310

Lys Ser Gly Met Phe Leu Thr Leu Phe Val Asn Thr Val Ile Asn
        2315                2320                2325

Ile Val Ile Ala Ser Arg Val Leu Arg Glu Arg Leu Thr Gly Ser
2330                2335                2340

Pro Cys Ala Ala Phe Ile Gly Asp Asp Asn Ile Val Lys Gly Val
        2345                2350                2355

Lys Ser Asp Lys Leu Met Ala Asp Arg Cys Ala Thr Trp Leu Asn
    2360                2365                2370

Met Glu Val Lys Ile Ile Asp Ala Val Val Gly Glu Lys Ala Pro
2375                2380                2385

Tyr Phe Cys Gly Gly Phe Ile Leu Cys Asp Ser Val Thr Gly Thr
        2390                2395                2400

Ala Cys Arg Val Ala Asp Pro Leu Lys Arg Leu Phe Lys Leu Gly
2405                2410                2415

Lys Pro Leu Ala Val Asp Glu His Asp Asp Asp Arg Arg Arg
        2420                2425                2430

Ala Leu His Glu Glu Ser Thr Arg Trp Asn Arg Val Gly Ile Leu
    2435                2440                2445

Pro Glu Leu Cys Lys Ala Val Glu Ser Arg Tyr Glu Thr Val Gly
        2450                2455                2460

Thr Ser Ile Ile Val Met Ala Met Thr Thr Leu Ala Ser Ser Val
    2465                2470                2475

Lys Ser Phe Ser Tyr Leu Arg Gly Ala Pro Ile Thr Leu Tyr Gly
        2480                2485                2490
```

<210> SEQ ID NO 24
<211> LENGTH: 557
<212> TYPE: PRT
<213> ORGANISM: Artificial Sequence
<220> FEATURE:
<223> OTHER INFORMATION: Synthetic sequence, VEEV TC-83 nsp3 E242K
<220> FEATURE:
<221> NAME/KEY: misc_feature
<222> LOCATION: (551)..(551)
<223> OTHER INFORMATION: Xaa can be any naturally occurring amino acid

<400> SEQUENCE: 24

```
Ala Pro Ser Tyr His Val Val Arg Gly Asp Ile Ala Thr Ala Thr Glu
1               5                   10                  15

Gly Val Ile Ile Asn Ala Ala Asn Ser Lys Gly Gln Pro Gly Gly Gly
                20                  25                  30

Val Cys Gly Ala Leu Tyr Lys Lys Phe Pro Glu Ser Phe Asp Leu Gln
            35                  40                  45

Pro Ile Glu Val Gly Lys Ala Arg Leu Val Lys Gly Ala Ala Lys His
        50                  55                  60

Ile Ile His Ala Val Gly Pro Asn Phe Asn Lys Val Ser Glu Val Glu
65                  70                  75                  80

Gly Asp Lys Gln Leu Ala Glu Ala Tyr Glu Ser Ile Ala Lys Ile Val
                85                  90                  95

Asn Asp Asn Asn Tyr Lys Ser Val Ala Ile Pro Leu Leu Ser Thr Gly
                100                 105                 110

Ile Phe Ser Gly Asn Lys Asp Arg Leu Thr Gln Ser Leu Asn His Leu
            115                 120                 125

Leu Thr Ala Leu Asp Thr Thr Asp Ala Asp Val Ala Ile Tyr Cys Arg
        130                 135                 140
```

-continued

Asp Lys Lys Trp Glu Met Thr Leu Lys Glu Ala Val Ala Arg Arg Glu
145                 150                 155                 160

Ala Val Glu Glu Ile Cys Ile Ser Asp Asp Ser Ser Val Thr Glu Pro
            165                 170                 175

Asp Ala Glu Leu Val Arg Val His Pro Lys Ser Ser Leu Ala Gly Arg
        180                 185                 190

Lys Gly Tyr Ser Thr Ser Asp Gly Lys Thr Phe Ser Tyr Leu Glu Gly
    195                 200                 205

Thr Lys Phe His Gln Ala Ala Lys Asp Ile Ala Glu Ile Asn Ala Met
210                 215                 220

Trp Pro Val Ala Thr Glu Ala Asn Glu Gln Val Cys Met Tyr Ile Leu
225                 230                 235                 240

Gly Lys Ser Met Ser Ser Ile Arg Ser Lys Cys Pro Val Glu Glu Ser
            245                 250                 255

Glu Ala Ser Thr Pro Pro Ser Thr Leu Pro Cys Leu Cys Ile His Ala
        260                 265                 270

Met Thr Pro Glu Arg Val Gln Arg Leu Lys Ala Ser Arg Pro Glu Gln
    275                 280                 285

Ile Thr Val Cys Ser Ser Phe Pro Leu Pro Lys Tyr Arg Ile Thr Gly
290                 295                 300

Val Gln Lys Ile Gln Cys Ser Gln Pro Ile Leu Phe Ser Pro Lys Val
305                 310                 315                 320

Pro Ala Tyr Ile His Pro Arg Lys Tyr Leu Val Glu Thr Pro Pro Val
            325                 330                 335

Asp Glu Thr Pro Glu Pro Ser Ala Glu Asn Gln Ser Thr Glu Gly Thr
        340                 345                 350

Pro Glu Gln Pro Pro Leu Ile Thr Glu Asp Glu Thr Arg Thr Arg Thr
    355                 360                 365

Pro Glu Pro Ile Ile Ile Glu Glu Glu Glu Asp Ser Ile Ser Leu
370                 375                 380

Leu Ser Asp Gly Pro Thr His Gln Val Leu Gln Val Glu Ala Asp Ile
385                 390                 395                 400

His Gly Pro Pro Ser Val Ser Ser Ser Trp Ser Ile Pro His Ala
            405                 410                 415

Ser Asp Phe Asp Val Asp Ser Leu Ser Ile Leu Asp Thr Leu Glu Gly
        420                 425                 430

Ala Ser Val Thr Ser Gly Ala Thr Ser Ala Glu Thr Asn Ser Tyr Phe
    435                 440                 445

Ala Lys Ser Met Glu Phe Leu Ala Arg Pro Val Pro Ala Pro Arg Thr
450                 455                 460

Val Phe Arg Asn Pro His Pro Ala Pro Arg Thr Arg Thr Pro Ser
465                 470                 475                 480

Leu Ala Pro Ser Arg Ala Cys Ser Arg Thr Ser Leu Val Ser Thr Pro
            485                 490                 495

Pro Gly Val Asn Arg Val Ile Thr Arg Glu Glu Leu Glu Ala Leu Thr
        500                 505                 510

Pro Ser Arg Thr Pro Ser Arg Ser Val Ser Arg Thr Ser Leu Val Ser
    515                 520                 525

Asn Pro Pro Gly Val Asn Arg Val Ile Thr Arg Glu Glu Phe Glu Ala
530                 535                 540

Phe Val Ala Gln Gln Gln Xaa Arg Phe Asp Ala Gly Ala
545                 550                 555